(12) United States Patent
Breaker

(10) Patent No.: US 6,630,306 B1
(45) Date of Patent: Oct. 7, 2003

(54) BIOREACTIVE ALLOSTERIC POLYNUCLEOTIDES

(75) Inventor: Ronald R. Breaker, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/849,069

(22) Filed: May 4, 2001

Related U.S. Application Data

(63) Continuation-in-part of application No. 09/331,809, filed as application No. PCT/US97/24158 on Dec. 18, 1997.
(60) Provisional application No. 60/033,684, filed on Dec. 19, 1996, and provisional application No. 60/055,039, filed on Aug. 8, 1997.

(51) Int. Cl.$^7$ .............. C12Q 1/68; C12M 1/34; G01N 33/566; C07H 21/04
(52) U.S. Cl. .............. 435/6; 435/196; 435/287.2; 536/23.1; 436/501
(58) Field of Search .............. 435/6, 287.2, 196; 536/23.1; 436/501

(56) References Cited

U.S. PATENT DOCUMENTS

| | | | |
|---|---|---|---|
| 5,143,854 A | | 9/1992 | Pirrung et al. |
| 5,445,934 A | | 8/1995 | Fodor et al. |
| 5,474,911 A | | 12/1995 | Pontius |
| 5,567,588 A | | 10/1996 | Gold et al. |
| 5,589,332 A | | 12/1996 | Shih et al. |
| 5,605,662 A | | 2/1997 | Heller et al. |
| 5,834,186 A | * | 11/1998 | George et al. |
| 6,001,067 A | * | 12/1999 | Shults et al. |
| 6,110,462 A | * | 8/2000 | Barbas et al. |

FOREIGN PATENT DOCUMENTS

| | | |
|---|---|---|
| WO | WO 94/13833 | 6/1994 |
| WO | WO 98/08974 | 3/1998 |

OTHER PUBLICATIONS

Bartel, D. and Szostak, J. (1993). *Science* 261: 1411–1418.
Kramer, F. and Lizardi, P. (1989). *Nature* 339: 401–402.
Pease, A. et al. (1994). *Proc. Natl. Acad. Sci. USA* 91: 5022–5026.
Porta, H. and Lizardi, P. (1995). *Bio/Technology* 13: 161–164.
Sargueil, B. et al. (1995). *Biochemistry* 34:7739–7748.
Schena, M. et al. (1996). *Proc. Natl. Acad. Sci. USA* 93: 10614–10619.
Yang, J. et al. (1992). *Biochemistry* 31: 5005–5009.
Breaker, R. and Joyce, G. (1994). *Chem. And Bio.* 1: 223–229.
Altman, et al., tRNA: Struc Biosyn Func, eds., Soll and RajBhandary: 67–78 (1995).
Berzal–Herranz, et al., Gen & Develop 6: 129–134 (1992).
Breaker, Curr Opin Biotech 7: 442–448 (1996).
Breaker and Joyce, Tren Biotech 12: 268–275 (1994).
Breaker and Joyce, Chem & Biol 2: 655–660 (1995).
Cech, Ann Rev Biochem 59: 543–568 (1990).
Christoffersen and Marr, J Med Chem 38: 2023–2037 (1995).
Cuenoud and Szostak, Nat 375: 611–614 (1995).
Fedor and Uhlenbeck, Biochemistry 31: 12042–12054 (1992).
Forster and Symons, Cell 49: 211–220 (1987).
Frank–Kamenetskii and Mirkin, Ann Rev Biochem 64: 65–95 (1995).
Gilbert, Nat 319: 618 (1986).
Gold, J Biol Chem 270(30): 13581–13584 (1995).
Gold, et al., Ann Rev Biochem 64: 763–797 (1995).
Hermann and Heumann, RNA 1: 1009–1017 (1995).
Herschlag and Cech, Nat 344: 405–409 (1990).
Hirao and Ellington, Curr Biol 5(9): 1017–1022 (1995).
Jenison, et al., Sci 263: 1425–1429 (1994).
Jose,et al., Nucleic Acids Res 29(7): 1631–1637 (2001).
Kazakov, et al., Nat 335: 186–188 (1988).
Koizumi, et al., Nat Struct Biol 6(11): 1062–1071 (1999).
Koizumi, et al., Nucl Acid Symp Ser 42: 275–276 (1999).
Li and Sen., Nat Struct Biol 3: 743–747 (1996).
Lim and Tole, J Am Chem Soc 114: 7245–7252 (1992).
Long and Uhlenbeck, Proc Natl Acad Sci USA 91: 6977–6981 (1994).
Michel and Ferat, Ann Rev Biochem 64: 435–461 (1995).
Perrreault and Anslyn, Angew Chem Int Ed Engl 36: 432–450 (1997).
Pley, et al., Nat 372: 68–74 (1994).
Robertson and Joyce, Nature 344: 467–468 (1990).
Sassanfar and Szostak, Nature 364: 550–553 (1993).
Scott, et al., Cell 81: 991–1002 (1995).
Seetharaman, et al., Nat Biotech 19: 336–341 (2001).
Serra and Turner, Meth Enzymol 259: 242–261 (1995).
Sigurdsson and Eckstein, Tren Biotech 13: 286–289 (1995).
Soukup, et al., RNA 7: 524–536 (2001).
Soukup, et al., J Mol Biol 298: 623–632 (2000).

(List continued on next page.)

*Primary Examiner*—Stephanie Zitomer
(74) *Attorney, Agent, or Firm*—Ivor R. Elrifi, Esq.; Mintz, Levin, Cohn, Ferris, Glovsky and Popeo, P.C.

(57) ABSTRACT

Polynucleotides having allosteric properties that modify a function or configuration of the polynucleotide with a chemical effector and/or physical signal are employed primarily as biosensors and/or enzymes for diagnostic and catalytic purposes. In some preferred embodiments, the polynucleotides are DNA enzymes that are used in solution/suspension or attached to a solid support as biosensors to detect the presence or absence of a compound, its concentration, or physical change in a sample by observation of self-catalysis. Chemical effectors include organic compounds such as amino acids, amino acid derivatives, peptides, nucleosides, nucleotides, steroids, and mixtures of these with each other and with metal ions, cellular metabolites or blood components obtained from biological samples, steroids, pharmaceuticals, pesticides, herbicides, food toxins, and the like. Physical signals include radiation, temperature changes, and combinations thereof.

24 Claims, 24 Drawing Sheets

OTHER PUBLICATIONS

Soukup and Breaker, Proc Natl Acad Sci USA 96: 3584–3589 (1999).
Soukup and Breaker, Structure 7: 783–791 (1999).
Soukup and Breaker, Tren Biotech 17: 469–476 (1999).
Strobel and Doudna, Tren Biochem Sci 22: 262–266 (1997).
Symons, Ann Rev Biochem 61: 641–671 (1992).
Tang and Breaker, Chem Biol 4: 453–459 (1997).
Tuschl, et al., Sci 266: 785–789 (1994).
Tuschl and Eckstein, Proc Natl Acad Sci USA 90: 6991–6994 (1993).
Tyagi and Kramer, Nat Biotech 14: 303–308 (1996).
Wladkowski, et al., J Am Chem Soc 117: 10537–10545 (1995).

* cited by examiner

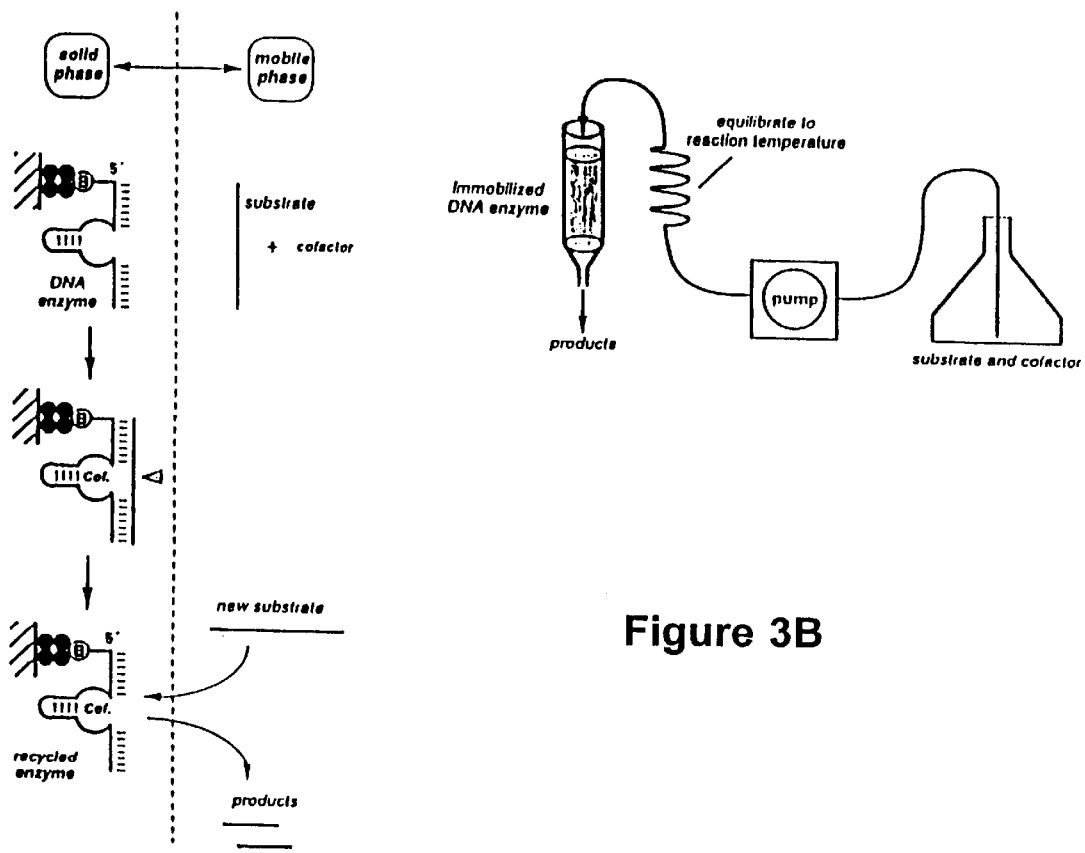
Figure 3B
Figure 3A
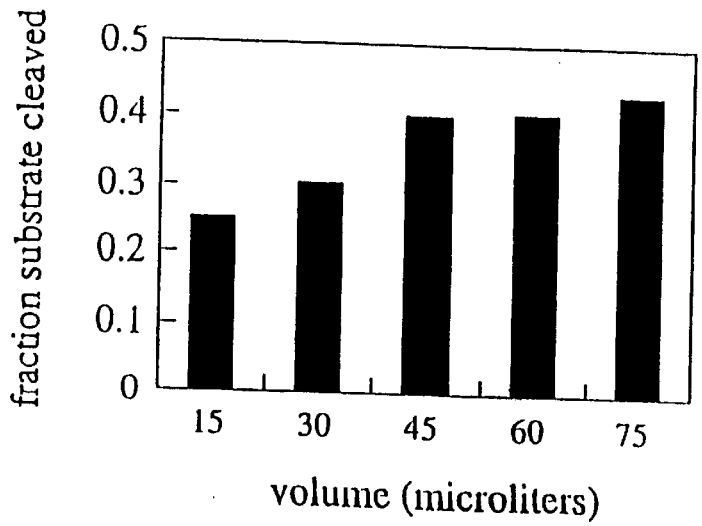
Figure 4

Figure 10A

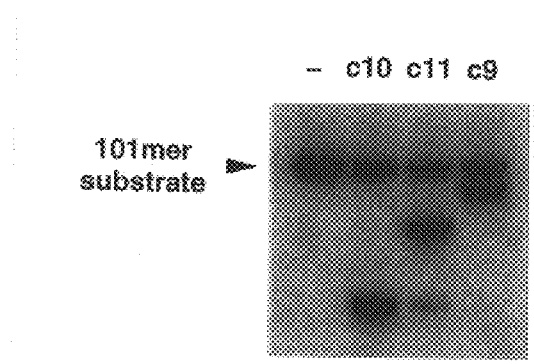
Figure 17D
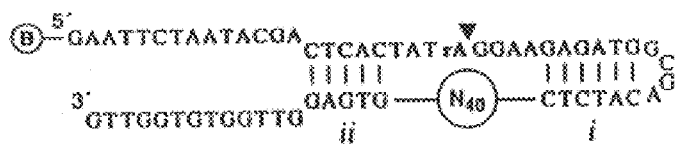
Figure 18A
|  |  |  | 10 | 20 | 30 | 40 | catalytic activity | |
|---|---|---|---|---|---|---|---|---|
| class | | | | | | | HEPES | histidine |
| I | (7) | GTTGGGTCAC | GGTATGGGGT | CACTCGACGA | AAATGCCGG | | + | + |
| II | (6) | AGGATTGGTT | CTGGGTGGGT | AGGAAGTTAG | TGTGAGCCG | | – | + |
| III | (4) | CGGGTCGAGG | TGGGAAAAC | AGGCAAGGCT | GTTCAGGATG | | + | + |
| IV | (3) | AGGATTAAGC | CGAATTCCAG | CACACTGGCG | GCCGCTTCAC | | + | + |
Figure 18B

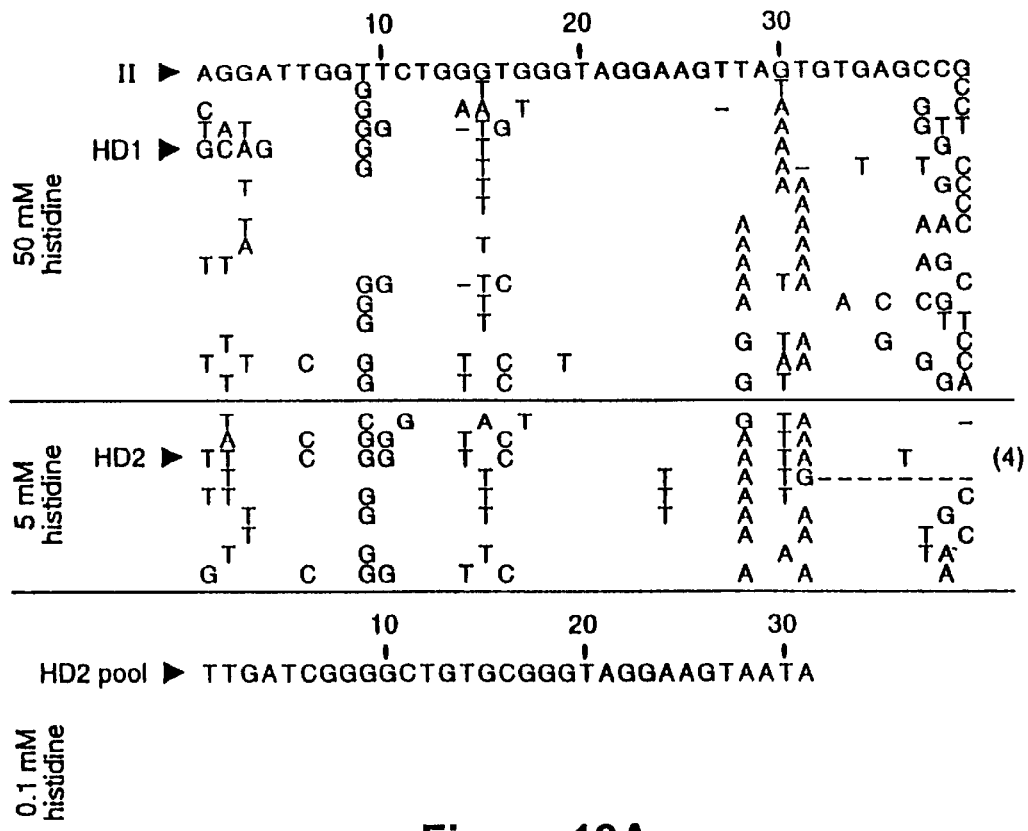
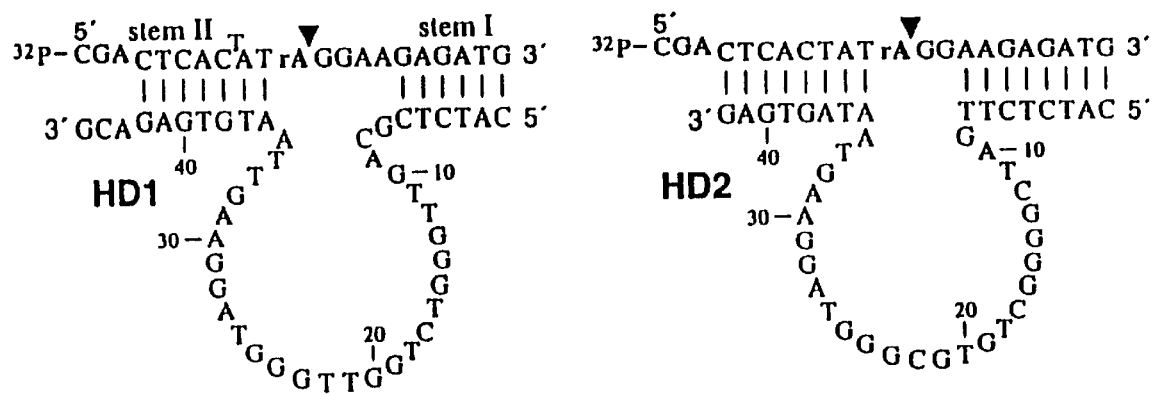
Figure 19A
Figure 19B

SEQUENCE LISTING

```
<160> NUMBER OF SEQ ID NOS: 57

<210> SEQ ID NO 1
<211> LENGTH: 46
<212> TYPE: DNA
<213> ORGANISM: artificial sequence
<220> FEATURE:
<223> OTHER INFORMATION: self-cleaving DNA

<400> SEQUENCE: 1
gaattctaat acgactcaaa gtgagtctgg gcctcttttt aagaac          46

<210> SEQ ID NO 2
<211> LENGTH: 34
<212> TYPE: RNA
<213> ORGANISM: artificial sequence
<220> FEATURE:
<223> OTHER INFORMATION: H1 ribozyme

<400> SEQUENCE: 2
ggcgaccctg augaggccga aaggccgaaa cggu                       34

<210> SEQ ID NO 3
<211> LENGTH: 56
<212> TYPE: RNA
<213> ORGANISM: artificial sequence
<220> FEATURE:
<223> OTHER INFORMATION: H2 ribozyme

<400> SEQUENCE: 3
ggcgaaagcc gggcgacccu gaugaggccg aaaggccgaa acgguagcga gagcuc    56

<210> SEQ ID NO 4
<211> LENGTH: 80
<212> TYPE: RNA
<213> ORGANISM: artificial sequence
<220> FEATURE:
<223> OTHER INFORMATION: H3 ribozyme

<400> SEQUENCE: 4
ggcgaaagcc gggcgacccu gaugaguugg gaagaaacug uggcacuucg          50
gugccagcaa cgaaacggua gcgagagcuc                                80

<210> SEQ ID NO 5
<211> LENGTH: 89
<212> TYPE: RNA
<213> ORGANISM: artificial sequence
<220> FEATURE:
<223> OTHER INFORMATION: H6 ribozyme

<400> SEQUENCE: 5
ggcgaaagcc gggcgacccu gaugaugagu guguggaag aaacuguggc            50 acuucggugc cagcguaugc gaaacgguag cgagagcuc                       89

<210> SEQ ID NO 6
<211> LENGTH: 77
<212> TYPE: RNA
```

```
<213> ORGANISM: artificial sequence
<220> FEATURE:
<223> OTHER INFORMATION: H8 ribozyme

<400> SEQUENCE: 6
gaaagccggg cgacccugau gaguugauac cagcacuucg gugcccuugg      50
cagcaacgaa acgguagcg agagcuc                                77

<210> SEQ ID NO 7
<211> LENGTH: 35
<212> TYPE: DNA
<213> ORGANISM: artificial sequence
<220> FEATURE:
<223> OTHER INFORMATION: primer 1

<400> SEQUENCE: 7
gtttcgcatt ggactaagtc ccaaccacac caacc                      35

<210> SEQ ID NO 8
<211> LENGTH: 38
<212> TYPE: DNA
<213> ORGANISM: artificial sequence
<220> FEATURE:
<223> OTHER INFORMATION: primer 2

<400> SEQUENCE: 8
gaattctaat acgactcact ataggaagag atggcgac                   38

<210> SEQ ID NO 9
<211> LENGTH: 49
<212> TYPE: DNA
<213> ORGANISM: artificial sequence
<220> FEATURE:
<223> OTHER INFORMATION: G8 DNA

<400> SEQUENCE: 9
gcagccaagg gtaggagctg gaggatgaca ggcggggtga taactagaa       49

<210> SEQ ID NO 10
<211> LENGTH: 49
<212> TYPE: DNA
<213> ORGANISM: artificial sequence
<220> FEATURE:
<223> OTHER INFORMATION: G8 DNA

<400> SEQUENCE: 10
ttatatagtc gagtccattc gaggtaggcg ggaacggtac tggtagaag       49

<210> SEQ ID NO 11
<211> LENGTH: 52
<212> TYPE: DNA
<213> ORGANISM: artificial sequence
<220> FEATURE:
<223> OTHER INFORMATION: G8 DNA

<400> SEQUENCE: 11
tctcacgtca ggagggtaga ctggtagcga taggcggcgg ggtgtaacag aa   52

<210> SEQ ID NO 12
<211> LENGTH: 50
<212> TYPE: DNA
<213> ORGANISM: artificial sequence
<220> FEATURE:
<223> OTHER INFORMATION: G8 DNA

<400> SEQUENCE: 12
```
agagctgtgg atctggagca aggaaatctcg gtaggcggg tttactagaa        50

<210> SEQ ID NO 13
<211> LENGTH: 48
<212> TYPE: DNA
<213> ORGANISM: artificial sequence
<220> FEATURE:
<223> OTHER INFORMATION: G8 DNA

<400> SEQUENCE: 13
gccagaacct ccgtaggcgg aaatgagtaaa cattgtaga agaggggg          48

<210> SEQ ID NO 14
<211> LENGTH: 45
<212> TYPE: DNA
<213> ORGANISM: artificial sequence
<220> FEATURE:
<223> OTHER INFORMATION: G8 DNA

<400> SEQUENCE: 14 gttagaacctc gtaggcgga aatgagtaaac atgtagaag agggg             45

<210> SEQ ID NO 15
<211> LENGTH: 50
<212> TYPE: DNA
<213> ORGANISM: artificial sequence
<220> FEATURE:
<223> OTHER INFORMATION: G8 DNA

<400> SEQUENCE: 15
gtttgaggga gacagatgtg gaaggcgggga gattgattc tctagaaggt        50

<210> SEQ ID NO 16
<211> LENGTH: 40
<212> TYPE: DNA
<213> ORGANISM: artificial sequence
<220> FEATURE:
<223> OTHER INFORMATION: G8 DNA

<400> SEQUENCE: 16
aggtaggcgg ggaatactaa cgctgttcagt attatagaa                   40

<210> SEQ ID NO 17
<211> LENGTH: 48
<212> TYPE: DNA
<213> ORGANISM: artificial sequence
<220> FEATURE:
<223> OTHER INFORMATION: G8 DNA

<400> SEQUENCE: 17 gtatgggta tatctgaagg cggaaatagct attgggctg ttgtagaa           48

<210> SEQ ID NO 18
<211> LENGTH: 50
<212> TYPE: DNA
<213> ORGANISM: artificial sequence
<220> FEATURE:
<223> OTHER INFORMATION: G8 DNA

<400> SEQUENCE: 18
agcaattcta ggataggcgg gaaagtggaat atgcgtttc agttgtagaa        50

<210> SEQ ID NO 19
<211> LENGTH: 48
<212> TYPE: DNA

```
<213> ORGANISM: artificial sequence
<220> FEATURE:
<223> OTHER INFORMATION: G8 DNA

<400> SEQUENCE: 19
attatggaag acagatgagg gcaggcgggaa tatacacat attaagaa                    48

<210> SEQ ID NO 20
<211> LENGTH: 43
<212> TYPE: DNA
<213> ORGANISM: artificial sequence
<220> FEATURE:
<223> OTHER INFORMATION: G8 DNA

<400> SEQUENCE: 20
tgataggcgg ctaaccctgc ttacgggttat ggttagtta gaa                         43

<210> SEQ ID NO 21
<211> LENGTH: 43
<212> TYPE: DNA
<213> ORGANISM: artificial sequence
<220> FEATURE:
<223> OTHER INFORMATION: G8 DNA

<400> SEQUENCE: 21
tgataggcgg gctaacctgc cttcgggttat ggttagtta gaa                         43

<210> SEQ ID NO 22
<211> LENGTH: 46
<212> TYPE: DNA
<213> ORGANISM: artificial sequence
<220> FEATURE:
<223> OTHER INFORMATION: G8 DNA

<400> SEQUENCE: 22
gtatagtgat ctcgggtctc tgtctatgaag aactgtagc cataat                      46

<210> SEQ ID NO 23
<211> LENGTH: 44
<212> TYPE: DNA
<213> ORGANISM: artificial sequence
<220> FEATURE:
<223> OTHER INFORMATION: G8 DNA

<400> SEQUENCE: 23
gtatagtgat ctggggtctg tctatgaagaa ctgtagcca taat                        44

<210> SEQ ID NO 24
<211> LENGTH: 50
<212> TYPE: DNA
<213> ORGANISM: artificial sequence
<220> FEATURE:
<223> OTHER INFORMATION: G8 DNA

<400> SEQUENCE: 24
gtaagggtgt ctgggtctct tctggggaaga actagagaa tgctgttggc                  50

<210> SEQ ID NO 25
<211> LENGTH: 49
<212> TYPE: DNA
<213> ORGANISM: artificial sequence
<220> FEATURE:
<223> OTHER INFORMATION: G8 DNA

<400> SEQUENCE: 25
ctgagtgata taggtgtctg ggtctcttatg acgaatgta attaagaac                   49
```

<210> SEQ ID NO 26
<211> LENGTH: 46
<212> TYPE: DNA
<213> ORGANISM: artificial sequence
<220> FEATURE:
<223> OTHER INFORMATION: G8 DNA

<400> SEQUENCE: 26
tgtttagaag caggctctta cttatcttctg ggcctctttt taagaa          46

<210> SEQ ID NO 27
<211> LENGTH: 47
<212> TYPE: DNA
<213> ORGANISM: artificial sequence
<220> FEATURE:
<223> OTHER INFORMATION: G8 DNA

<400> SEQUENCE: 27
tgtttagagg caggctctta atgcttctggg cctctttttt taagaac         47

<210> SEQ ID NO 28
<211> LENGTH: 49
<212> TYPE: DNA
<213> ORGANISM: artificial sequence
<220> FEATURE:
<223> OTHER INFORMATION: G8 DNA

<400> SEQUENCE: 28
gtgagaagtt tcaattggac gtgagtctggg tctctttgc gtgaagaac          49

<210> SEQ ID NO 29
<211> LENGTH: 39
<212> TYPE: DNA
<213> ORGANISM: artificial sequence
<220> FEATURE:
<223> OTHER INFORMATION: G8 DNA

<400> SEQUENCE: 29
tgtttagaac gaggctccta cttctggcctc ttttagac                    39

<210> SEQ ID NO 30
<211> LENGTH: 50
<212> TYPE: DNA
<213> ORGANISM: artificial sequence
<220> FEATURE:
<223> OTHER INFORMATION: C1 DNA

<400> SEQUENCE: 30
atagttaaga gcgcgtggta ggcgggaaca aatgtttacg ttgtgtagaa         50

<210> SEQ ID NO 31
<211> LENGTH: 50
<212> TYPE: DNA
<213> ORGANISM: artificial sequence
<220> FEATURE:
<223> OTHER INFORMATION: C3 DNA

<400> SEQUENCE: 31
tgtttagaag caggctctta cttatgcttc tgggcctctt ttttaagaac         50

<210> SEQ ID NO 32
<211> LENGTH: 87
<212> TYPE: DNA
<213> ORGANISM: artificial sequence
<220> FEATURE:

<223> OTHER INFORMATION: C1 variant DNA

<400> SEQUENCE: 32
gaattctaat acgactcact ataggaagag atggcgacat agttaagagc          50
tcggggtagg cgggaacaac gttcacgttg tgtagaa                        87

<210> SEQ ID NO 33
<211> LENGTH: 69
<212> TYPE: DNA
<213> ORGANISM: artificial sequence
<220> FEATURE:
<223> OTHER INFORMATION: self-cleaving DNA

<400> SEQUENCE: 33
gaattctaat acgactcact ataggaagag atggcgacct agattgagtc          50
tgggcctctt tttaagaac                                            69

<210> SEQ ID NO 34
<211> LENGTH: 46
<212> TYPE: DNA
<213> ORGANISM: artificial sequence
<220> FEATURE:
<223> OTHER INFORMATION: truncated class II DNA

<400> SEQUENCE: 34 gaattctaata cgactcaga atgagtctgg gcctcttttt aagaac              46

<210> SEQ ID NO 35
<211> LENGTH: 21
<212> TYPE: DNA
<213> ORGANISM: artificial sequence
<220> FEATURE:
<223> OTHER INFORMATION: S3 DNA

<400> SEQUENCE: 35
gaattctaat acggcttacc g                                         21

<210> SEQ ID NO 36
<211> LENGTH: 28
<212> TYPE: DNA
<213> ORGANISM: artificial sequence
<220> FEATURE:
<223> OTHER INFORMATION: C3 DNA

<400> SEQUENCE: 36
cggtaagcct gggcctcttt taagaac                                   28

<210> SEQ ID NO 37
<211> LENGTH: 65
<212> TYPE: DNA
<213> ORGANISM: artificial sequence
<220> FEATURE:
<223> OTHER INFORMATION: DNA with 3 cleavage sites

<400> SEQUENCE: 37
gtcgacctgc gagctcgact catacgtcga tccctcatgt ggcttaccga          50
agctttacga tctac                                                65

<210> SEQ ID NO 38
<211> LENGTH: 58
<212> TYPE: DNA
<213> ORGANISM: artificial sequence
<220> FEATURE:
<223> OTHER INFORMATION: DNA with 3 cleavage sites

```
<400> SEQUENCE: 38 gtcgacctgcg agctttctc ttgctcttct ttgcttcttt ctaagcttta          50
cgatctac                                                        58

<210> SEQ ID NO 39
<211> LENGTH: 44
<212> TYPE: DNA
<213> ORGANISM: artificial sequence
<220> FEATURE:
<221> NAME/KEY: misc_RNA
<222> LOCATION: 20...22
<223> OTHER INFORMATION: portion 1
      n is an RNA A linkage

<400> SEQUENCE: 39
gaattctaat acgactcact nggaagagat ggcgacacac tctc                44

<210> SEQ ID NO 40
<211> LENGTH: 18
<212> TYPE: DNA
<213> ORGANISM: artificial sequence
<220> FEATURE:
<223> OTHER INFORMATION: portion 2

<400> SEQUENCE: 40
gtgaggttgg tgtggttg                                             18

<210> SEQ ID NO 41
<211> LENGTH: 39
<212> TYPE: DNA
<213> ORGANISM: artificial sequence
<220> FEATURE:
<221> NAME/KEY: misc_RNA
<222> LOCATION: 20...22
<223> OTHER INFORMATION: class I DNA

<400> SEQUENCE: 41
gttgggtcac ggtatggggt cactcgacga aaatgccgg                      39

<210> SEQ ID NO 42
<211> LENGTH: 39
<212> TYPE: DNA
<213> ORGANISM: artificial sequence
<220> FEATURE:
<223> OTHER INFORMATION: class II DNA

<400> SEQUENCE: 42
aggattggtt ctgggtgggt aggagttag tgtgatccg                       39

<210> SEQ ID NO 43
<211> LENGTH: 40
<212> TYPE: DNA
<213> ORGANISM: artificial sequence
<220> FEATURE:
<223> OTHER INFORMATION: class III DNA

<400> SEQUENCE: 43
cgggtcgagg tggggaaaac aggcaaggct gttcaggatg                     40

<210> SEQ ID NO 44
<211> LENGTH: 40
<212> TYPE: DNA
<213> ORGANISM: artificial sequence
<220> FEATURE:
<223> OTHER INFORMATION: class IV DNA
```

<400> SEQUENCE: 44
aggattaagc cgaattccag cacactggcg gccgcttcac        40

<210> SEQ ID NO 45
<211> LENGTH: 38
<212> TYPE: DNA
<213> ORGANISM: artificial sequence
<220> FEATURE:
<223> OTHER INFORMATION: class II DNA

<400> SEQUENCE: 45
aggattggtt ctgggtgggt aggaagttag tgtgagcc          38

<210> SEQ ID NO 46
<211> LENGTH: 31
<212> TYPE: DNA
<213> ORGANISM: artificial sequence
<220> FEATURE:
<223> OTHER INFORMATION: HD2 pool DNA

<400> SEQUENCE: 46
ttgatcgggg ctgtgcgggt aggaagtaat a                 31

<210> SEQ ID NO 47
<211> LENGTH: 66
<212> TYPE: DNA
<213> ORGANISM: artificial sequence
<220> FEATURE:
<221> NAME/KEY: misc_RNA
<222> LOCATION: 9...11
<223> OTHER INFORMATION: HD1
    n is an RNA A linkage

<400> SEQUENCE: 47
cgactcacat nggaagagat gcatctcgca gttgggtctg gttgggtagg    50
aagttaatgt gagacg                                         66

<210> SEQ ID NO 48
<211> LENGTH: 65
<212> TYPE: DNA
<213> ORGANISM: artificial sequence
<220> FEATURE:
<221> NAME/KEY: misc_RNA
<222> LOCATION: 11...13
<223> OTHER INFORMATION: HD2
    n is an RNA A linkage

<400> SEQUENCE: 48
cgactcacta tngaagaga tgcatctctt gatcggggc tgtgcgggta     50 ggaagtaata gtgag                                         65

<210> SEQ ID NO 49
<211> LENGTH: 39
<212> TYPE: DNA
<213> ORGANISM: artificial sequence
<220> FEATURE:
<223> OTHER INFORMATION: primer

<400> SEQUENCE: 49
gaattctaat acgactcacta taggcgaaag ccgggcga         39

<210> SEQ ID NO 50
<211> LENGTH: 16
<212> TYPE: DNA

```
<213> ORGANISM: artificial sequence
<220> FEATURE:
<223> OTHER INFORMATION: primer

<400> SEQUENCE: 50 gagctctcg ctaccgt                                                      16

<210> SEQ ID NO 51
<211> LENGTH: 18
<212> TYPE: DNA
<213> ORGANISM: artificial sequence
<220> FEATURE:
<223> OTHER INFORMATION: primer

<400> SEQUENCE: 51
gtcgacctgc gagctcga                                                    18

<210> SEQ ID NO 52
<211> LENGTH: 18
<212> TYPE: DNA
<213> ORGANISM: artificial sequence
<220> FEATURE:
<223> OTHER INFORMATION: primer

<400> SEQUENCE: 52
gtagatcgta aagcttcg                                                    18

<210> SEQ ID NO 53
<211> LENGTH: 38
<212> TYPE: DNA
<213> ORGANISM: artificial sequence
<220> FEATURE:
<223> OTHER INFORMATION: template, part 1

<400> SEQUENCE: 53
ctaatacgac tcactatagg aagagatggc gacatctc                              38

<210> SEQ ID NO 54
<211> LENGTH: 18
<212> TYPE: DNA
<213> ORGANISM: artificial sequence
<220> FEATURE:
<223> OTHER INFORMATION: template, part 2

<400> SEQUENCE: 54
gtgaggttgg tgtggttg                                                    18

<210> SEQ ID NO 55
<211> LENGTH: 23
<212> TYPE: DNA
<213> ORGANISM: artificial sequence
<220> FEATURE:
<221> NAME/KEY: misc_RNA
<222> LOCATION: end
<223> OTHER INFORMATION: primer
      n is an RNA A

<400> SEQUENCE: 55
gaattctaat acgactcact atn                                              23

<210> SEQ ID NO 56
<211> LENGTH: 18
<212> TYPE: DNA
<213> ORGANISM: artificial sequence
<220> FEATURE:
<223> OTHER INFORMATION: primer
```

```
<400> SEQUENCE: 56
caaccacacc aacctcac                                              18

<210> SEQ ID NO 57
<211> LENGTH: 38
<212> TYPE: DNA
<213> ORGANISM: artificial sequence
<220> FEATURE:
<223> OTHER INFORMATION: primer

<400> SEQUENCE: 57
gaattctaat acgactcact ataggaagag atggcgac                        38
```

BIOREACTIVE ALLOSTERIC POLYNUCLEOTIDES

CROSS-REFERENCES TO RELATED APPLICATIONS

This application is a continuation-in-part of co-pending U.S. application Ser. No. 09/331,809, filed Jun. 18, 1999 as a national phase entry of PCT/US97/24158, filed internationally Dec. 18, 1997 and claiming priority benefit of U.S. application Ser. No. 60/033,684, filed Dec. 19, 1996 and Ser. No. 60/055,039, filed Aug. 8, 1997.

STATEMENT REGARDING FEDERALLY SPONSORED RESEARCH

The invention was made with partial government support under NIH grant GM59343. The government has certain rights in the invention.

BACKGROUND OF THE INVENTION

1. Field of the Invention

This invention relates primarily to functional DNA polynucleotides that exhibit allosteric properties, and to catalytic RNA and DNA polynucleotides that have catalytic properties with rates that can be controlled by a chemical effector, a physical signal, or combinations thereof. Bioreactive allosteric polynucleotides of the invention are useful in a variety of applications, particularly as biosensors.

Biosensors are widely used in medicine, veterinary medicine, industry, and environmental science, especially for diagnostic purposes. Biosensors are typically composed of a biological compound (sensor material) that is coupled to a transducer, in order to produce a quantitative readout of the agent or conditions under analysis. Usually, the biological component of the biosensor is a macromolecule, often subject to a conformational change upon recognition and binding of its corresponding ligand. In nature, this effect may immediately initiate a signal process (e.g., ion channel function in nerve cells). Included in the group of 'affinity sensors' are lectins, antibodies, receptors, and oligonucleotides. In biosensors, ligand binding to the affinity sensor is detected by optoelectronic devices, potentiometric electrodes, field effect transistors (FETs), or the like.

Alternatively, the specificity and catalytic power of proteins have been harnessed to create biosensors that operate via enzyme function. Likewise, proteins have been used as immobilized catalysts for various industrial applications. The catalytic activity of purified enzymes or even whole organelles, microorganisms or tissues can be monitored by potentiometric or amperometric electrodes, FETs, or thermistors. The majority of biosensors that are commercially available are based on enzymes, of which the oxidoreductases and lyases are of great interest. It is nearly exclusively the reactants of the reactions catalyzed by these enzymes for which transducers are available. These transducers include potentiometric electrodes, FETs, pH- and $O_2$-sensitive probes, and amperometric electrodes for $H_2O_2$ and redox mediators. For example, the oxidoreductases, a group of enzymes that catalyze the transfer of redox equivalents, can be monitored by detectors that are sensitive to $H_2O_2$ or $O_2$ concentrations.

Enzymes are well-suited for application in sensing devices. The binding constants for many enzymes and receptors can be extremely low (e.g., avidin; $K_d = 10^{-15}$ M) and the catalytic rates are on the order of a few thousand per second, but can reach 600,000 $sec^{-1}$ (carboanhydrase) (45). Enzymes can be monitored as biosensors via their ability to convert substrate to product, and also be the ability of certain analytes to act as inhibitors of catalytic function.

Organic chemistry and biochemistry have reached a state of proficiency where new molecules can be made to simulate the function of protein receptors and enzymes. Macrocyclic rings, polymers for imprinting, and self-assembling monolayers are now being intensively investigated for their potential application in biosensors. In addition, the immune system of animals can be harnessed to create new ligand-binding proteins that can act as artificial biorecognition systems. Antibodies that have been made to bind transition-state analogues can also catalyze chemical reactions, thereby functioning as novel 'artificial enzymes' (36). The latter examples are an important route to the creation of biosensors that can be used to detect non-natural compounds, or that function under non-physiologic conditions.

2. Description of Related Art

In nature, RNA not only serves as components of the information transfer process, but also performs tasks that are typically accomplished by proteins, including molecular recognition and catalysis. A seemingly endless variety of aptamers, and even DNA aptamers can be created in vitro that bind various ligands with great affinity and specificity (17). Nucleic acids likely have an extensive and as yet untapped ability adopt specific conformations that can bind ligands and also to catalyze chemical transformations (16). The engineering of new RNA and DNA receptors and catalysts is primarily achieved via in vitro selection, a method by which trillions of different oligonucleotide sequences are screened for molecules that display the desired function. This method consists of repeated rounds of selection and amplification in a manner that simulates Darwinian evolution, but with molecules and not with living organisms (4). One drawback to the use of existing enzymes as biosensors is that one is limited to developing a sensor based on the properties of existing enzymes or receptors. A significant advantage can be gained if one could 'tailor-make' the sensor for a particular application. It would be desirable to employ nucleic acids to create entirely new biosensors that have properties and specificities that span beyond the range of capabilities of current biosensors.

In vitro selection has been the main vehicle for new ribozyme discoveries in recent years. The catalytic repertoire of ribozymes includes RNA and DNA phosphoester hydrolysis and transesterification, RNA ligation, RNA phosphorylation, alkylation, amide and ester bond formation, and amide cleavage reactions. Recent evidence has shown that biocatalysis is not solely the realm of RNA and proteins. DNA has been shown to form catalytic structures that efficiently cleave RNA (5,7), that ligate DNA (10), and that catalyze the metallation of porphyrin rings (24). As described herein, self-cleaving DNAs have been isolated from a random-sequence pool of molecules that operate via a redox mechanism, making possible the use of an artificial DNA enzyme in place of oxidoreductase enzymes in biosensors. In addition, these DNA enzymes or 'deoxyribozymes' are considerably more stable that either RNA or protein enzymes—an attractive feature for the sensor component of a biosensor device.

BRIEF SUMMARY OF THE INVENTION

It is an object of the invention to provide examples of RNA and DNA sensing elements for use in biosensors, including polynucleotides attached to a solid support. Both RNA and DNA can be designed to bind a variety of ligands with considerable specificity and affinity. In addition, both RNA and DNA can be made to catalyze chemical trans formations under user-defined conditions. A combination of rational design and combinatorial methods has been used to create prototype biosensors based on RNA and DNA.

These and other objects of the invention are accomplished by the present invention, which provides purified functional DNA polynucleotides that exhibit allosteric properties that modify a function or configuration of the polynucleotide with a chemical effector, a physical signal, or combinations thereof. The invention further provides purified functional polynucleotides having catalytic properties with rates that can be controlled by a chemical effector, a physical signal, or combinations thereof. Some embodiments are enzymes exhibiting allosteric properties that modify the rate of catalysis of the enzyme. In addition, the invention encompasses biosensors comprising bioreactive allosteric polynucleotides described herein.

Examples of chemical effectors include, but are not limited to, organic compounds such as amino acids, amino acid derivatives, peptides, nucleosides, nucleosides, nucleotides, steroids, and mixtures of organic compounds and metal ions. In some embodiments, the effectors are microbial or cellular metabolites or components of bodily fluids such as blood and urine obtained from biological samples. In other embodiments, the effectors are pharmaceuticals, pesticides, herbicides, and food toxins. Physical signals include, but are not limited to, radiation and temperature changes.

The invention also provides methods for determining the presence or absence of compounds, or compound concentrations in biological, industrial, and environmental samples, and physical changes in such samples using bioreactive allosteric polynucleotides of the invention and biosensors incorporating them.

DESCRIPTION OF THE FIGURES

FIG. 3 sketches an example of (A) an immobilized DNA biocatalyst of the invention and (B) a simple reactor assembly.

FIG. 4 shows a demonstration of catalytic function by immobilized DNA enzymes. 5' $^{32}$P-labeled RNA substrate was applied to a streptavidin column (AffiniTip Strep 20, Genosys Biotechnologies) that was derivatized with 5'-biotinyl DNA enzyme. The DNA enzyme was immobilized to give an effective concentration of ~1 $\mu$M. Substrate (0.5 $\mu$M was applied to the column in repetitive 20 $\mu$L aliquots, allowed to react for 10 min., then recovered for analysis by polyacrylamide gel electrophoresis. Fraction of substrate cleaved was plotted as a function of volume eluted.

above. Miscleavage is detected for each triplex-guided deoxyribozyme upon extended exposure during autoradiography (e.g., c11), indicating that weak-forming triplex interactions allow some DNA-cleavage activity to occur.

FIG. 18 illustrates the in vitro selection of histidine-dependent deoxyribozymes described in Example 4. (a) A pool of $4 \times 10^{13}$ biotin-modified DNAs was immobilized on a streptavidin-derivatized column matrix. Each DNA carries a single embedded RNA linkage (rA) and a 40-nucleotide random-sequence domain that is flanked by regions that are complementary to nucleotides that reside both 5' and 3' of the target phosphodiester (pairing elements i and ii; SEQ ID NOs: 39 and 40). These pre-engineered substrate-binding interactions are expected to increase the probability of isolating active catalysts (7). DNAs that catalyze the cleavage of the RNA linkage upon incubation with a solution buffered with histidine were released from the matrix, were amplified by the polymerase chain reaction (PCR), and the amplification products again were immobilized to complete the selection cycle (14–16). (b) Four classes of deoxyribozymes were determined by sequence comparison (SEQ ID NOs 41 to 44). Variants within each group differed by no more that two mutations from the sequences shown. Catalytic assays active (+) when either HEPES or histidine buffers are used, while class II DNAs not active (–) when histidine is absent. Arrowhead identifies the site of cleavage and numbers correspond to the original 40-nucleotide random-sequence domain.

FIG. 19 shows sequences and secondary structures of variant deoxyribozymes discussed in Example 4. (a) Individual DNAs isolated after reselection of mutagenized pools based on the class II deoxyribozyme (II) (SEQ ID NO: 45) or the HD2 deoxyribozyme (HD2 pool, SEQ ID NO: 46). Depicted are the nucleotide sequences for the mutagenized core of the parent DNAs and the nucleotide changes for each variant deoxyribozyme examined after reselection. Deoxyribozymes HD1 (SEQ ID NO: 47) and HD2 (SEQ ID NO: 48) were recovered from DNA pools generated after five rounds of reselection with 50 or 5 mM histidine, respectively. (b) Each deoxyribozyme was reorganized to create a bimolecular complex, whereby separate substrate molecules are recognized by two regions of base complementation (stems I and II) with the enzyme domain. Deoxyribozyme nucleotides are numbered consecutively from the 5' terminus.

Figure 20A:
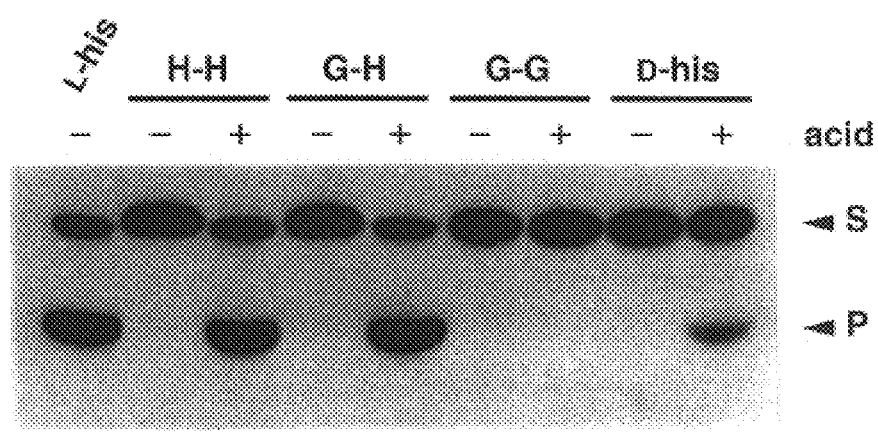
Figure 20B:
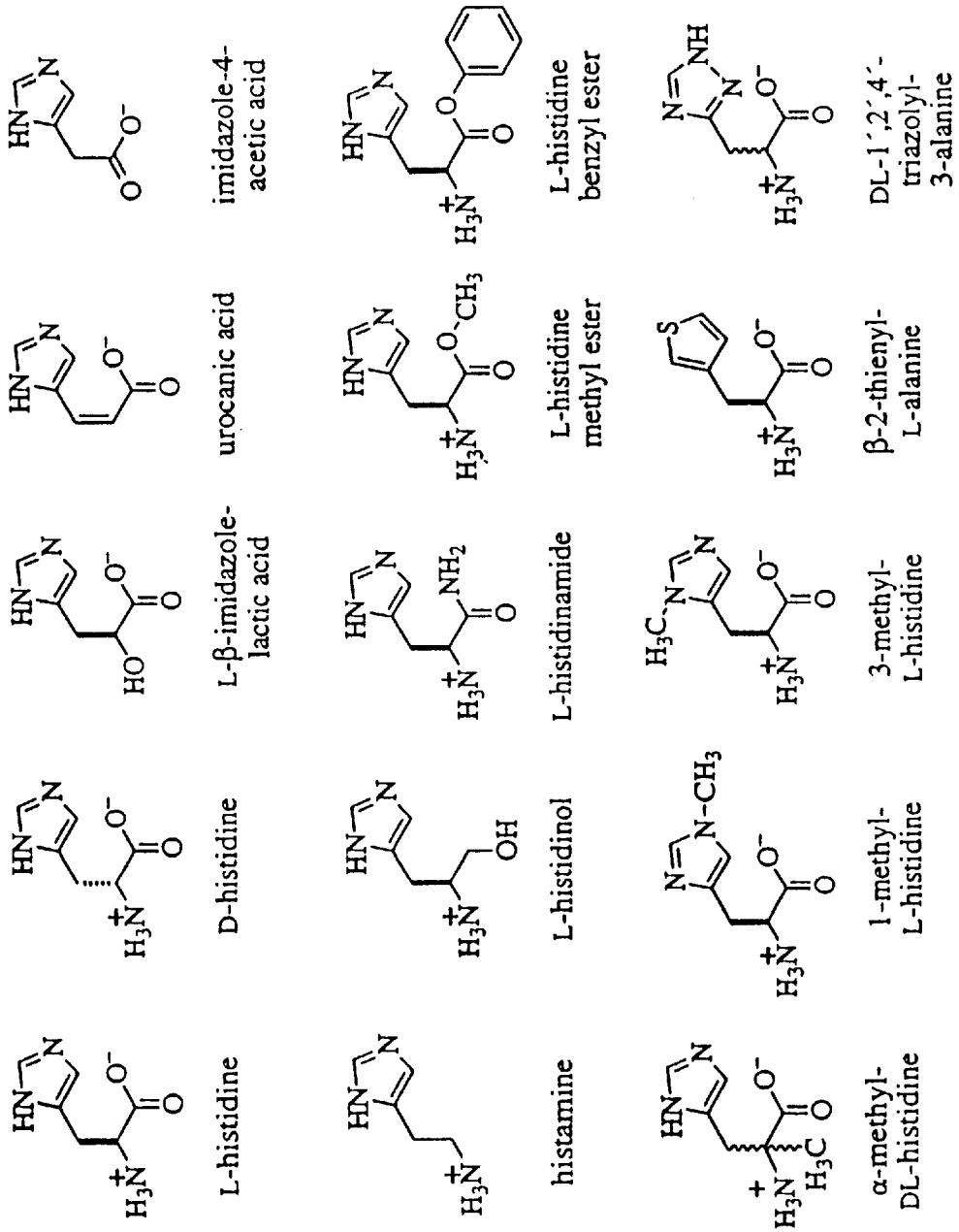
Figure 20C:
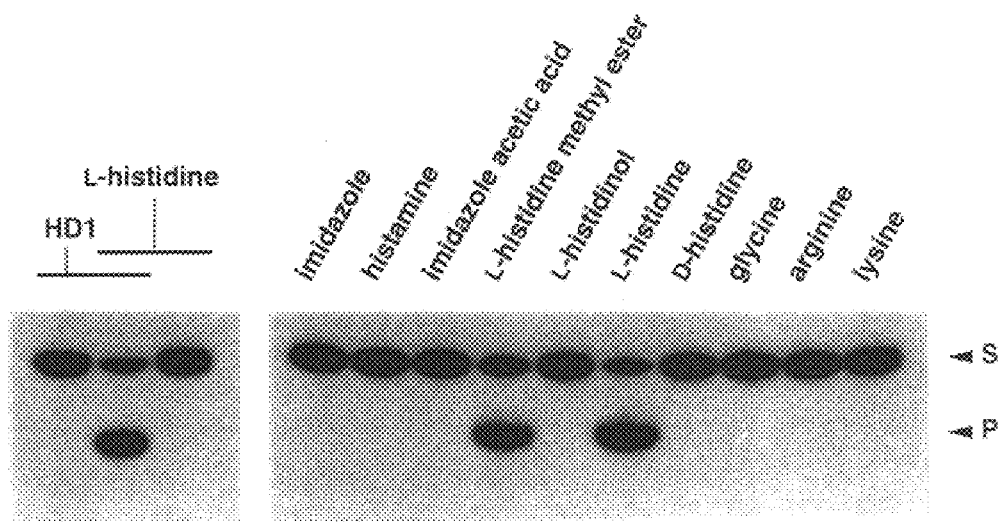

FIG. 20 shows cofactor recognition by a deoxyribozyme described in Example 4. (a) Catalytic activity of HD1 with L-histidine, D-histidine, and various dipeptides that received (+) or did not receive (–) pretreatment with hydrochloric acid. HD1 (10 µM) was incubated in the presence of trace amounts of 5' $^{32}$P-labeled substrate oligonucleotide (FIG. 19b) and were incubated at 23° C. for 2.5 hr with 50 mM L-histidine, D-histidine, or various dipeptides as indicated. Reaction products were analyzed by denaturing (8 M urea) polyacrylamide gel electrophoresis (PAGE) and imaged by autoradiography. S and P identify substrate and product (5'-cleavage fragment) bands, respectively. (b) Chemical structures of L-histidine and the analogues used to probe deoxyribozyme cofactor specificity. (c) Representative deoxyribozyme assays for HD1 (E1) catalytic activity with selected amino acids and histidine analogues. Reactions and analyses were conducted as described in a.

Figure 21A:
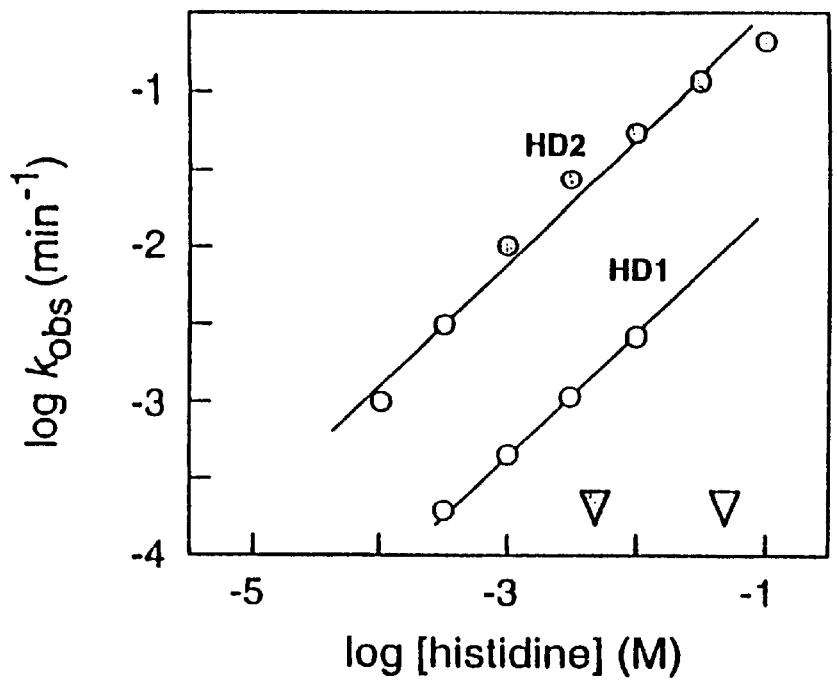

FIG. 21 are graphs showing the involvement of histidine in deoxyribozyme function described in Example 4. (a) Concentration-dependent induction of deoxyribozyme function by histidine. Open and shaded arrowheads indicate the concentration of histidine that was maintained during the selection of HD1 and HD2, respectively. (b) Dependence of deoxyribozyme function on pH. Data represented in the main plot was produced using 1 mM histidine while data given in the inset was obtained using 5 mM histidine. Data depicted with filled, open, and shaded circles was collected using MES-, Tris-, and CAPS-buffered solutions, respectively.

DETAILED DESCRIPTION OF THE INVENTION

Natural ribozymes and artificial ribozymes and deoxyribozymes that have been isolated by in vitro selection are not known to operate as allosteric ribozymes. This invention is based upon the finding that small-molecule effectors can bind to ribozyme and deoxyribozyme domains and modulate catalytic rate. As will be discussed more fully below, in the practice of the invention, an effector molecule or effect binds or affects an allosteric site that is spatially distinct from that of the enzyme or reporter domain. Allosteric polynucleotides of the invention can thus rapidly interconvert from an "off" state to an "on" state, or vice versa, reversibly, on a time scale that is relevant for their use as biosensors and bioswitches. For example, using rational design strategies, a 'hammerhead' self-cleaving ribozyme described herein was coupled to different aptamer domains to produce ribozymes whose rates can be specifically controlled by adenosine and it's 5'-phosphorylated derivatives. A number of other allosteric ribozymes have been created that are sensitive to a variety of other effectors, including drug compounds, biological metabolites, and toxic metals. It is possible to construct, using a mix of in vitro selection and rational design strategies, novel biosensors that rely on nucleic acid sensor elements. To achieve this, unique RNA or DNA sequences can be appended to ribozymes or deoxyribozymes, thereby creating new enzymes having catalytic rates that can be influenced by specific chemical effectors (e.g., molecules.of diagnostic interest), physical signals, and combinations thereof.

About 50 years ago, it was observed with some polypeptide enzymes that catalytic plots of reaction velocity, V, versus substrate concentration [S], displayed sigmoidal plots, rather than hyperbolic plots predicted by the simple enzyme + substrate model of enzymatic action described by Michaelis-Menten in 1913. In 1965, Monod, et al., explained these findings by suggesting that enzymatic reaction rates were altered by regulatory domains (3a). In this classical model of "allostery", enzymatic activity by "allosteric enzymes" is modulated by reversible binding to compounds, termed "effectors", at specific sites other than the enzyme's substrate binding sites, which, accordingly, are called "allosteric" sites. At constant enzyme and substrate concentrations, binding of a negative "effector" reduces the reaction rate ("allosteric inhibition"), and binding of a positive "effector", increases the rate, ("allosteric activation"). Allosteric inhibition may be achieved a number of ways, including reducing the binding affinity of the enzyme for its substrate (often reported as increases in Michaelis-Menton parameter $K_m$) and/or by increasing the time required for each catalytic turnover (often reported as a decrease in $V_{max}$). Conversely, allosteric activation may occur either by reduction in $K_m$ or by an increase in $V_{max}$, or both.

Decades later it was found that polynucleotides could also catalyze chemical reactions, and in 1995, Porta and Lizardi described what they called the first "allosteric" ribozyme (32a). This was a hammerhead, self-cleaving ribozyme that could be rendered active by incubating it with a 35-nucleotide antisense DNA oligomer for several hours. Notwithstanding the terminology used in the paper, this was not a true allosteric effect. Antisense interactions such as that described between the oligonucleotide and the ribozyme are typically comprised of strong base pairing contacts that have slow kinetic interchange between bound and unbound states. There was no allosteric interconversion (from an "off" state to an "on" state, or vice versa) disclosed upon addition of the 35-mer to an ongoing reaction mixture. Instead, Porta and Lizardi described a ribozyme construct which had a folding pathway that could be dictated by the 35-mer, but not allosterically switched from active to inactive forms immediately upon addition or depletion of a small effector molecule to or from the reaction mixture. Hence, their need for long preincubation and incubation times, and a large oligonucleotide that could kinetically and thermodynamically lock the ribozyme into an active configuration.

In contrast, in the practice of the invention, purified functional DNA and/or polynucleotides that exhibit true allosteric properties that modify a function or configuration of the polynucleotide with a chemical effector, a physical signal, or combinations thereof, are constructed. The function of polynucleotides of the invention is not necessarily controlled by base pairing to an oligonucleotide, but, instead, by binding of a small molecule effector to an allosteric binding site, or interaction of a physical signal with an allosteric site, spatially distinct from the enzyme domain, such that the function of the polynucleotide is allosterically modulated. In some embodiments, the polynucleotide is an enzyme exhibiting allosteric properties that modify the rate of catalysis of the enzyme. The invention further provides functional RNA or DNA polynucleotides having catalytic properties with rates that can be positively and/or negatively controlled by a chemical effector, a physical signal, or combinations thereof. For example, where enzyme polynucleotides of the invention exhibit a reaction rate that is enhanced or inhibited by reversible binding to a chemical effector at an allosteric binding site spatially distinct from the substrate binding or self-cleaving site. In some embodiments, the polynucleotides contain from about 100 or fewer bases; others are much larger.

Allosteric, polynucleotides of the invention are comprised of any natural, recombinant, or synthetic RNA, DNA and mixtures of RNA and DNA. As used herein, the terms "DNA" and "RNA" specifically include sequences that have RNA and/or DNA analogues. Analogues include chemically modified bases and unusual natural bases. Further encompassed by the invention are polynucleotides modified during or after preparation of the domains and constructs using standard means. DNA and/or RNA starting materials for the domains, and constructs and complexes containing them, may be isolated from whole organisms, tissues or tissue cultures; constructed from nucleotides and oligonucleotides using standard means; obtained commercially; selected from random and enriched in vitro or in vivo sequence pools; and combinations thereof.

Any element, ion, and/or molecule can be used as chemical effectors for interaction with the bioreactive allosteric polynucleotides of the invention. It is an advantage of the invention that the rational design strategies used to construct the polynucleotides (discussed more fully below) can be adapted to a great variety of effectors. A vast number of ligand-responsive ribozymes with dynamic structural characteristics can be generated in a massively parallel fashion (23b). Examples include, but are not limited to, organic compounds and mixtures of organic compounds and metal ions. Chemical effectors may be amino acids, amino acid derivatives, peptides (including peptide hormones), polypeptides, nucleosides, nucleotides, steroids, sugars or other carbohydrates, pharmaceuticals, and mixtures of any of these. Many are small; hence, peptides having 9 or fewer amino acid substitutents and disaccharides and trisaccharides are typical polypeptide and carbohydrate effectors. Illustrated hereafter are theophylline, ATP and modified ATP; 3-methylxanthine, cGMP, cCMP, cAMP, FMN, cobalt, cadmium, nickel, zinc, and manganese have also been shown to be effectors that modulate the reaction rates of polynucleotides of the invention (see, for example, various effectors described in 21a, 23a, 23b, 36a, 39a, 39b, 39c, and 39e). In many preferred embodiments, small molecule effectors, typically having a molecular weight of about 300 or less; are employed, including metal ions, amino acids, amino acid derivatives, nucleosides, nucleotides, simple sugars, and steroids. Effectors can be much larger in other embodiments; larger molecule effectors can have molecular weights ranging in the tens or thousands Da, and sometimes even larger; protein effectors, for example, can range up to 500,000, and sometimes several million, Da. In some embodiments, the chemical effectors are microbial or cellular metabolites or other biological samples. Components found in liquid biological samples such blood, serum, urine, semen, tears, and biopsy homogenates taken from patients for medical or veterinary diagnostic or therapeutic purposes are particularly preferred chemical effectors in some embodiments (36a). In industrial and environmental applications, the effectors are pesticides, herbicides, food toxins, product ingredients, reactants, and contaminants, drugs, and the like. Allosteric polynucleotides of the invention can be used to detect the presence or absence of compounds, as well as their concentration (36a).

Figure 7A:
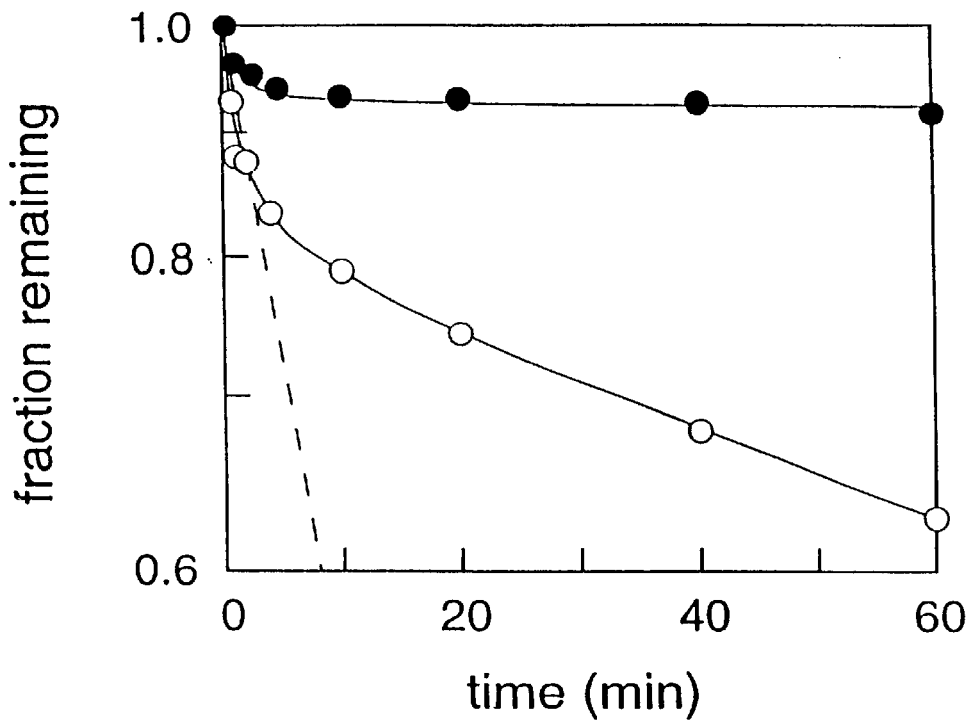
FIG. 7 plots kinetic analysis results of the catalytic inhibition of H3 by ATP described in Example 1. (A) Plot of H3 ribozyme activity (400 mM) in the presence of 10 $\mu$M (open circles) and 1 mM (filled circles) ATP. Dashed line represents the average initial slope obtained in the absence of ATP or in the presence of as much as 1 mM dATP. (B) Plot of H3 ribozyme activity ($k_{obs}$) in the presence of various concentrations of dATP (open circles) and ATP (filled circles). Also plotted on the y axis are $k_{obs}$ values for H1, H2 and H3 (open squares, filled squares and open circles, respectively) with no added effector molecules.
Figure 7B:
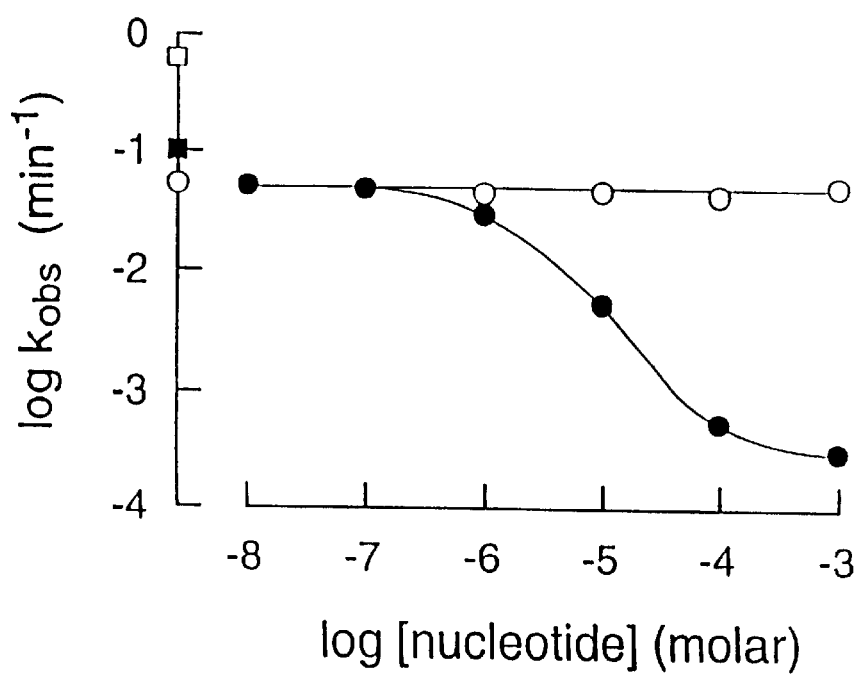
Figure 8A:
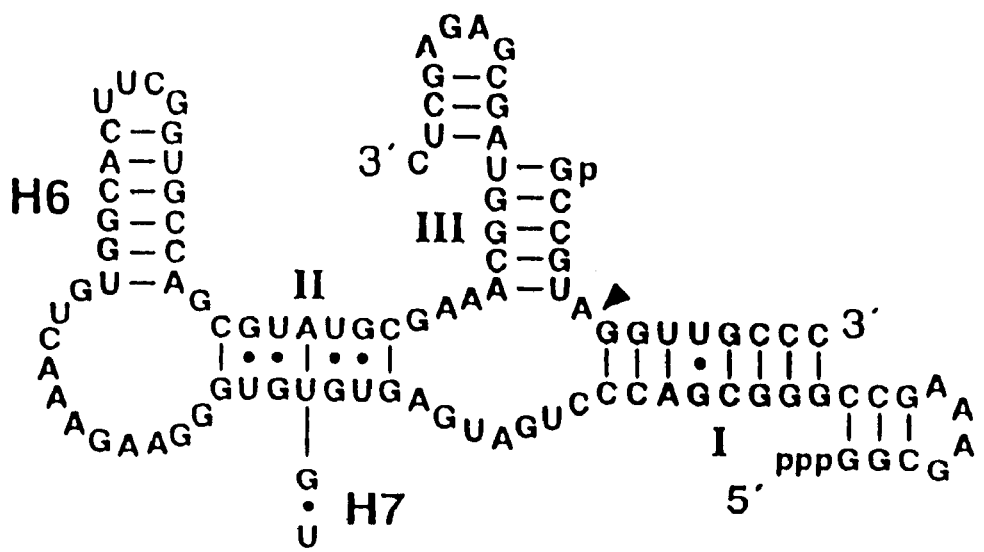
FIG. 8(A) depicts integrated constructs for allosteric induction by ATP (H6, SEQ ID NO: 5 and H7, SEQ ID NO: 6) and allosteric inhibition by theophilline (H8) described in Example 1. H7 replaces the central U–A pair with a $G_oU$ mismatch and is designed to further reduce hammerhead catalysis. H8 is analogous to H3 except that the ATP-aptamer domain is replaced by the theophylline aptamer corresponding to 'mTCT8-4' that was described by Jenison, et al. (21). Arrowhead indicates the site of ribozyme-mediated cleavage. (B) Induction of ribozyme catalysis during the course of a ribozyme reaction was examined by incubating H6 in the absence (open circles) and presence (open squares) of 1 mM ATP, and when ATP is added (filled circles), to a final concentration of 1 mM during an ongoing ribozyme reaction. Arrow indicates the time of ATP addition.
Figure 8A:
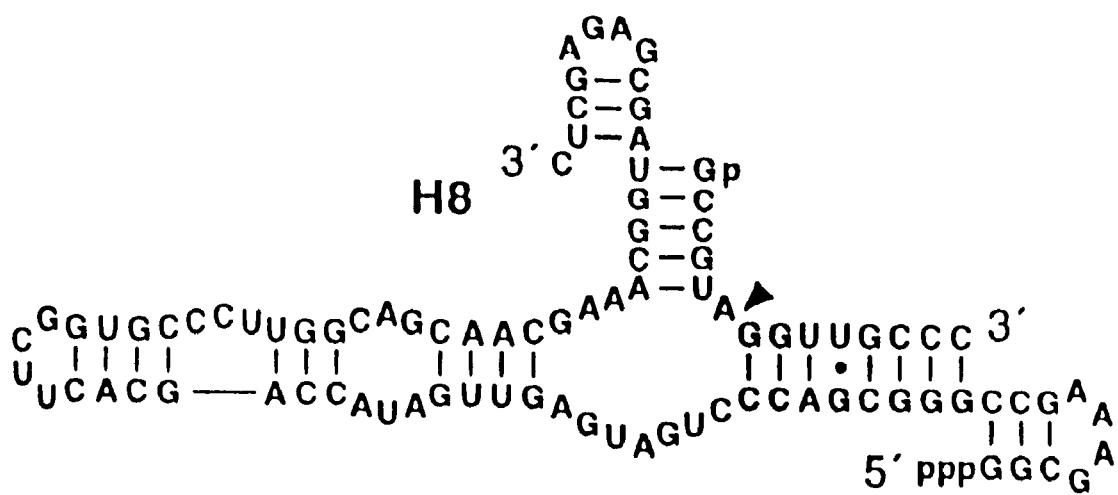

Bioreactive polynucleotides of the invention exhibit allosteric properties that modify polymer function or configuration with a physical signal or a combination of a physical signal and a chemical effector in alternate embodiments. Physical signals include, but are not limited to, radiation (23a), temperature changes, movement, physical conformational changes in samples, and combinations thereof. Physical signals include, but are not limited to, tags, beacons, and the like allosteric reporters that respond to UV, IR, and/or visible light (23b, 44b). The effects are reversible. Chemical effectors binding to allosteric ribozymes and/or deoxyribozymes of the invention, for example, can enhance or inhibit the catalytic rate, or do both. It is an advantage of the invention that, because the molecules are truely allosteric, any type of allosteric interconversion is possible. Hence, a sample of allosteric polynucleotide enzymes can be fully active, partially active, or fully inactive. In other words, acting as a switch, they can be all "on" or all "off", or exhibit any level of activity between "on" or "off" . (For a further discussion of switches, see Soukup and Breaker, 39c). Morever, because they are truly allosteric, the observable response time to an effector molecule or effect is immediate. The kinetics of allosteric polynucleotides are similar to what is observed with allosteric polypeptides. Illustrated hereafter are polynucleotides that react in less than 60 minutes, preferably inless than 6 minutes, and most preferably, in less than about a minute. (See, for example, FIGS. 7 and 8.) Most preferred allosteric polynucleotides respond to effectors within seconds.

Figure 1:
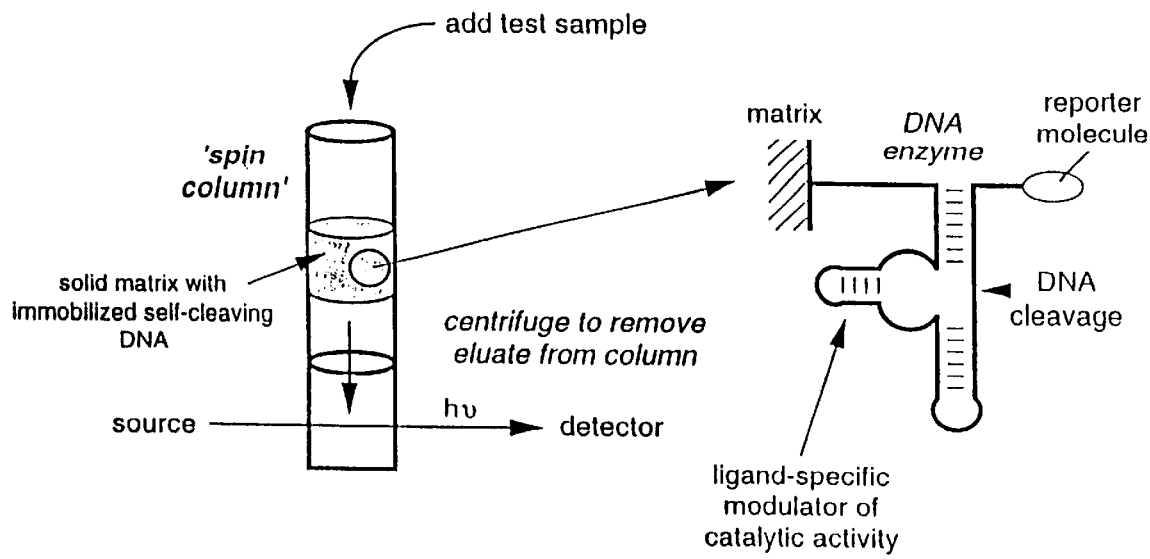
FIG. 1 is a schematic diagram of an example of a biosensor of the invention. In this embodiment, a self-cleaving DNA is immobilized on a solid matrix that is mounted in a plastic 'spin-column'. The self-cleaving DNA remains inactive, unless it encounters a specific effector molecule that causes allosteric induction. Test sample is added to the porous matrix, allowed to incubate, then the solution is collected at the bottom of the tube via centrifugation. Since catalytic activity is a function of the presence (in concentration) of the effector, the concentration of released DNA fragments will report the presence and quantity of effector.

Many embodiments employ bioreactive allosteric polynucleotides of the invention as biosensors in solution or suspension or attached to a solid support such as that illustrated in FIG. 1. Alone or as a component of a biosensor, the polynucleotides are used to detect the presence or absence of a compound or its concentration and/or a physical signal by contact with the polynucleotide. In a typical practice of these methods, a sample is incubated with the polynucleotide or biosensor comprising the polynucleotide as a sensing element for a time under conditions sufficient to observe a modification or configuration of the polynucleotide caused by the allosteric interaction. These are monitored using any method known to those skilled in the art, such as measurement and/or observation of polynucleotide self-cleavage; binding of a radioactive, fluorescent, or chromophoric tag; binding of a monoclonal or fusion phage antibody; or change in component concentration, spectrophotometric, or electrical properties. It is an advantage of the invention that current biosensor technology employing potentiometric electrodes, FETs, various probes, redox mediators, and the like can be adapted for use in conjunction with the new polynucleotide biosensors of the invention for measurement of changes in polynucleotide function or configuration.

The initial studies described in the Examples that follow have involved the creation and characterization of novel RNA- and DNA-cleaving enzymes that function with specific cofactors, or that can be regulated by specific small-molecule chemical effectors, physical signals, or combinations thereof. It is clear that additional molecules with similar sensor and biocatalytic properties can be created by similar means, thereby expanding the applications of such molecules. The creation and characterization of a prototype biosensor for ATP is given herein. One construct (H3) in particular shows ATP concentration-dependent catalytic activity, indicating that this ribozyme could be adapted for use in reporting the concentration of this ligand in test solutions. Specifically, H3 RNA actively self-cleaves in concentrations of ATP that are below 1 micromolar, but is maximally inhibited (170-fold rate reduction) in the presence of 1 millimolar ATP (FIG. 3b). The catalytic rate of the ribozyme in concentrations of ATP that range between these two extremes is reflective of the ATP concentration, and can be used to determine unknown concentration values. It is important to note that the receptor portion of this allosteric ribozyme is completely artificial (created via in vitro selection) (35), and could be exchanged for other artificial or natural receptor domains that are specific for other ligands.

New and highly-specific receptors can be made via in vitro selection or 'SELEX' (4,5) using simple chromatographic and nucleic acid amplification techniques (4, and illustrated in the Examples). RNA and DNA 'aptamers' produced in this way can act as efficient and selective receptors for small organic compounds, metal ions, and even large proteins. In a dramatic display of RNA receptor function, a series of RNA aptamers for theophilline have been isolated (35) that show ~10,000-fold discrimination against caffeine, which differs from theophilline by a single methyl group.

One can isolate new classes of aptamers that are specific for innumerable compounds to create novel biosensors or even controllable therapeutic ribozymes for use in medical diagnostics, environmental analysis, etc. In the examples that follow, simple design strategies have been used to create conjoined aptamer-ribozyme complexes who's rates can be controlled by small effector molecules. Preliminary studies have already shown that theophilline-dependent ribozymes can be created through rational design. Theophilline, for example, is an important drug for the treatment of asthma and it's therapeutic effect is highly dependent on concentration. A biosensor for theophilline concentration would be of significant value. Further examination of this allosteric ribozyme and of other model ribozymes will help to lay the biochemical and structural foundations for the design of additional sensor molecules based on RNA and DNA.

It is an advantage of the invention that the discovery that DNA can function as an enzyme (5) has made practical the engineering of enzymes that are chemically more stable than either RNA or proteins. The half-life for the hydrolytic breakdown of a DNA phosphoester is ~200 million years, making DNA the most stable of the three major biopolymers. These features of DNA, coupled with the fact that DNA also can be made to bind various ligand with great specificity and affinity, make this polymer an attractive medium for the creation of new industrial enzymes and as sensor elements for diagnostics. Also, modified DNAs can be made that are resistant to degradation by natural nucleases, making DNA analogues an attractive format for use in biological solutions. As illustrated hereafter, it has been found that DNA can be made to self-cleave in a metal ion-dependent fashion. The creation of these DNAs that catalyze their own cleavage in the presence of copper can now be used as a sensitive reporter of free copper concentration in solution. Another example given below is a polynucleotide reactive to histidine. Further engineering of such catalysts will yield allosteric DNA enzymes that can be used to detect a wide variety of ligands, or that report other reaction conditions such as the concentration of salts, pH, temperature, etc. In addition, these DNAs may be conducive to monitoring via amperometric $H_2O_2$ probes or by spectrophotometric analysis of the redox state of copper. Clearly, the diversity of signal read-out for both RNA and DNA sensors can be expanded.

Another feature of the invention is that use of polynucleotides as biosensors offer advantages over protein-based enzymes in a number of commercial and industrial processes. Problems such as protein stability, supply, substrate specificity and inflexible reaction conditions all limit the practical implementation of natural biocatalysts. As outlined above, however, DNA can be engineered to operate as a catalyst under defined reactions conditions. Moreover, catalysts made from DNA are expected to be much more stable and can be easily made by automated oligonucleotide synthesis. In addition, DNA catalysts are already selected for their ability to function on a solid support and are expected to retain their activity when immobilized.

The invention further encompasses the use of bioreactive allosteric polynucleotides attached to a solid support for use in catalytic processes. Immobilizing novel DNA enzymes will provide a new form of enzyme-coated surfaces for the efficient catalysis of chemical transformations in a continuous-flow reactor under both physiological and non-physiological conditions. The isolation of new DNA enzymes, can be each tailor-made to efficiently catalyze specific chemical transformations under user-defined reaction conditions. The function of catalytic DNAs to create enzyme-coated surfaces that can be used in various catalytic processes is described herein and illustrated in FIG. 4. Due to the high stability of the DNA phosphodiester bond, such surfaces are expected to remain active for much longer than similar surfaces that are be coated with protein- or RNA-based enzymes.

A variety of different chromatographic resins and coupling methods can be employed to immobilize DNA enzymes. For example, a simple non-covalent method that takes advantage of the strong binding affinity of streptavidin for biotin to carry out a model experiment is illustrated in FIG. 3. In other embodiments, DNA enzymes can be coupled to the column supports via covalent links to the matrix, thereby creating a longer-lived catalytic support. Various parameters of the system including temperature, reaction conditions, substrate and cofactor concentration, and flow rate can be adjusted to give optimal product yields. In fact, these parameters can be preset based on the kinetic characteristic that are displayed by the immobilized DNA enzyme. However, in practice, product formation will be monitored and the chromatographic parameters will be adjusted accordingly to optimize the system.

A prototype system for the large-scale processing of RNA substrates using an immobilized DNA enzyme is described herein. Product yields have been determined by analysis of $^{32}$P-labeled substrate and product molecules by polyacrylamide gel electrophoresis of eluant samples. Multiple turnover of immobilized enzyme during tests of the reactive chromatographic surface has been observed (FIG. 4). The in vitro selection and engineering of new tailor-made DNA biocatalysts will produce catalytic surfaces for practical use and of unprecedented stability and catalytic versatility.

EXAMPLES

The following examples are presented to further illustrate and explain the present invention and should not be taken as limiting in any regard.

Example 1

As mentioned above, natural ribozymes (8) and ribozymes that have been isolated by in vitro selection are not known to operate as allosteric enzymes (6). This example illustrates allosteric ribozymes.

Using simple rational design concepts, aptamer domains with hammerhead self-cleaving ribozymes (13) were joined in a modular fashion, to create a series of catalytic RNAs that are amenable to both positive and negative allosteric control by small-molecule effectors. Initial efforts were focused on the 40-nucleotide ATP-binding aptamer, termed 'ATP-40-1', that was described by Sassanfar and Szostak (35). This motif shows a specific affinity for adenosine 5' triphosphate ATP; $K_D$~10 $\mu$M) and adenosine, but has no detected affinity for a variety of ATP analogues including 2'-deoxyadenosine 5' triphosphate (dATP) or the remaining three natural ribonucleoside triphosphates. The aptamer also undergoes a significant conformational. change upon ligand binding, as determined by chemical probing studies. These characteristics were exploited to create a conjoined aptamer-ribozyme molecule that could be subject to ATP-dependent allosteric control.

Figure 5:
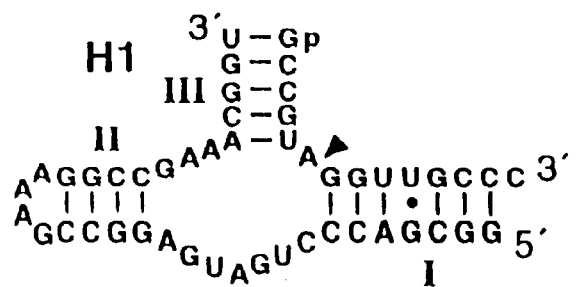
FIG. 5 illustrates hammerhead ribozyme constructs described in Example 1 below. H1 (SEQ ID NO: 2) is identical to the ribozyme 'HH15' that was originally characterized by Fedor and Uhlenbeck (12). H2 (SEQ ID NO: 3) carries an additional G–C base pair in stem I and is flanked on each end by accessory sequences that are designed as short hairpins to reduce the occurance of inactive structures. H3 (SEQ ID NO: 4) is an integrated hammerhead riboizyme that includes an RNA domain corresponding to a truncated version of an ATP- and adenosine-specific aptamer (35). H4 and H5 are modified versions of H3 that include an aptamer-domain mutation and a 3 base-pair extension of stem II, respectively. Arrowheads indicate the site of ribozyme-mediated cleavage.
Figure 5:
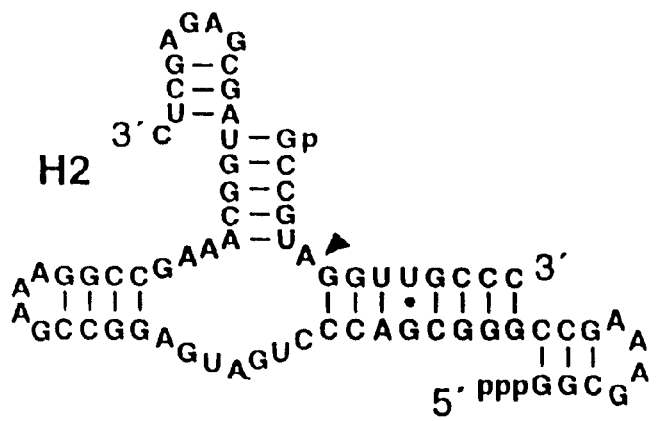
Figure 5:
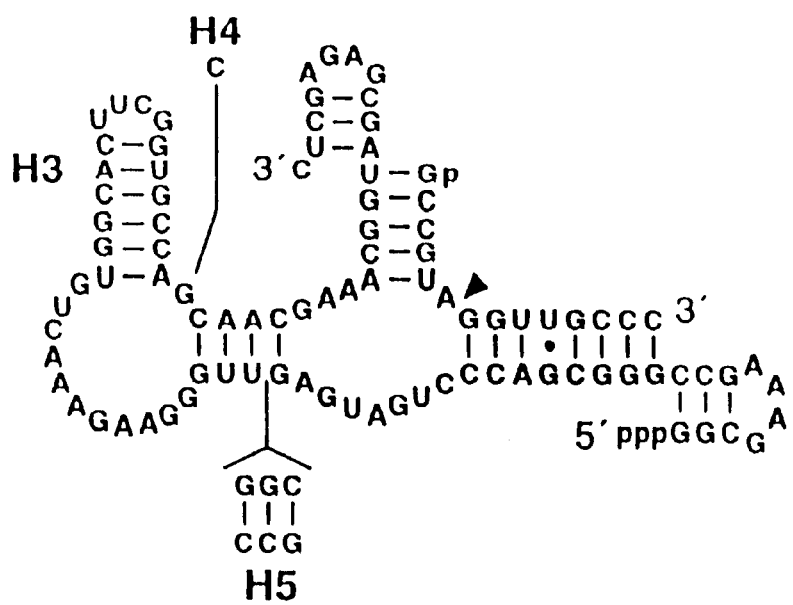

The initial integrated design, H3, incorporates several key features into an otherwise unaltered bimolecular hammerhead ribozyme that is embodied by H1 (FIG. 5). Each ribozyme and conjoined aptamer-ribozyme was prepared by in vitro transcription from a double-stranded DNA template that was produced by the polymerase chain reaction using the corresponding antisense DNA template and the primers 5' GAATTCTAATACGACTCACTATAGGC-GAAAGCCGGGCGA (SEQ ID NO: 49) and 5' GAGCTCTCGCTACCGT (SEQ ID NO: 50). The former primer encodes the promoter for T7 RNA polymerase. 50-$\mu$l transcription reactions were performed by incubating of 30 pmoles template DNA in the presence of 50 mM Tris-HCl (pH 7.5 at 23° C.), 15 mM MgCl$_2$, 5 mM dithiothreitol, 2 mM spermidine, 2 mM of each NTP, 20 $\mu$Ci ($\alpha$-$^{32}$P-UTP and 600 units T7 RNA polymerase for 2 hr at 37° C. RNA products were separated by polyacrylamide gel electrophoresis (PAGE), visualized by autoradiography and the ribozymes were recovered from excised gel slices by crush-soaking in 10 mM Tris-HCl (pH 7.5 at 23° C.), 200 mM NaCl and 1 mM EDTA and quantified by liquid scintillation counting. The RNA substrate was prepared (Keck Biotechnology Resource Laboratory, Yale University) by standard solid-phase methods and the 2'-TBDMS group was removed by 24-hr treatment with triethylamine trihydrofluoride (15 $\mu$l per AU$_{260}$ crude RNA). Substrate RNA was purified by PAGE, isolated by crush-soaking, (5'-$^{32}$P)-labeled with T4 polynucleotide kinase and ($\gamma$-$^{32}$P)-ATP, and repurified by PAGE. Even after exhaustive incubation with H1, approximately 45% of the RNA remains uncleaved. The kinetic calculations have been adjusted accordingly.

Superficially, sequences at the 5' and 3' termini were appended to make the constructs amenable to amplification by reverse transcription-polymerase chain reaction methods for future studies. Surveyed independently as H2 (FIG. 5), these changes causes a 6-fold reduction in k$_{obs}$ compared to H1 (rates are summarized in Table 1). In addition to the 5'- and 3'-terminal flanking sequences, H3 includes a modified hammerhead stem II that carries the ATP aptamer. The decision to locate the aptamer here was made primarily because changes in stem II can have large effects on the catalytic rates of hammerhead ribozymes (28). In the absence of ATP, this alteration causes an additional two-fold reduction in rate compared to H1.

Figure 2:
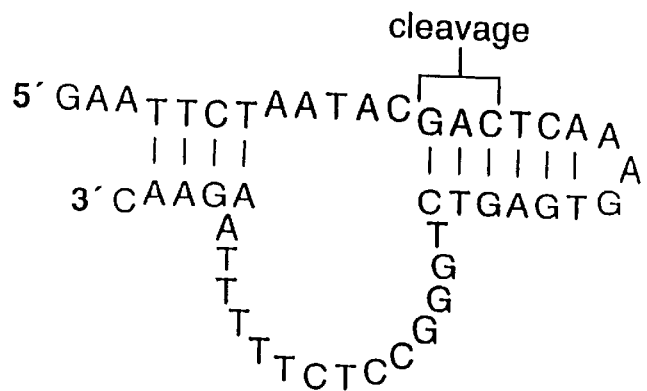
FIG. 2 illustrates a sequence and secondary-structure model for a self-cleaving DNA of the invention (SEQ ID NO: 1). The bracket indicates the main region of DNA cleavage.
Figure 6A:
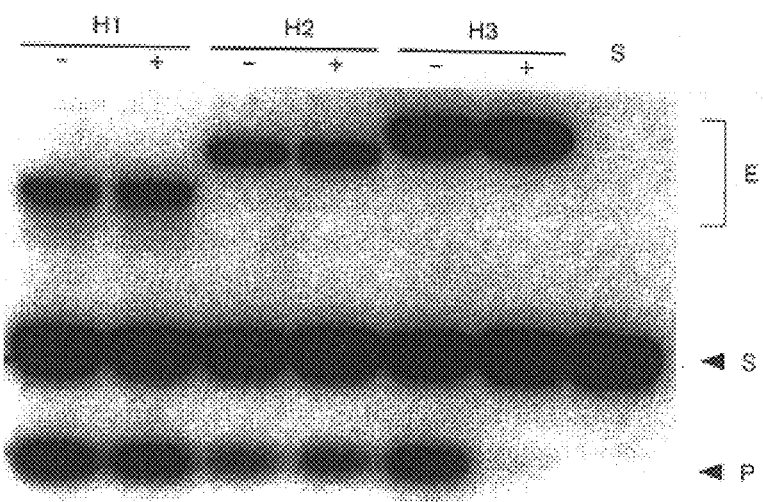
FIG. 6 shows evidence of ATP- and adenosine-mediated inhibition of a hammerhead ribozyme described in Example 1. (A) Hammerhead constructs H1, H2 and H3 (400 nM) were incubated with trace amounts of (5'-$^{32}$P)-labeled substrate (S) in the absence (−) or presence (+) of 1 mM ATP for 30 min. (B) The specificity of the effector molecule was examined by incubating H3 and S for 45 min as described in Example 1 without (−) or with 1 mM of various nucleotides as indicated. Similarly, constructs H4 and H5 were examined for activity in the presence of 1 mM ATP. Reaction products were separated by a denaturing (8 M urea) 20% polyacrylamide gel and visualized by autoradiography. E, S and P identify enzyme, substrate and product bands, respectively.
Figure 6B:
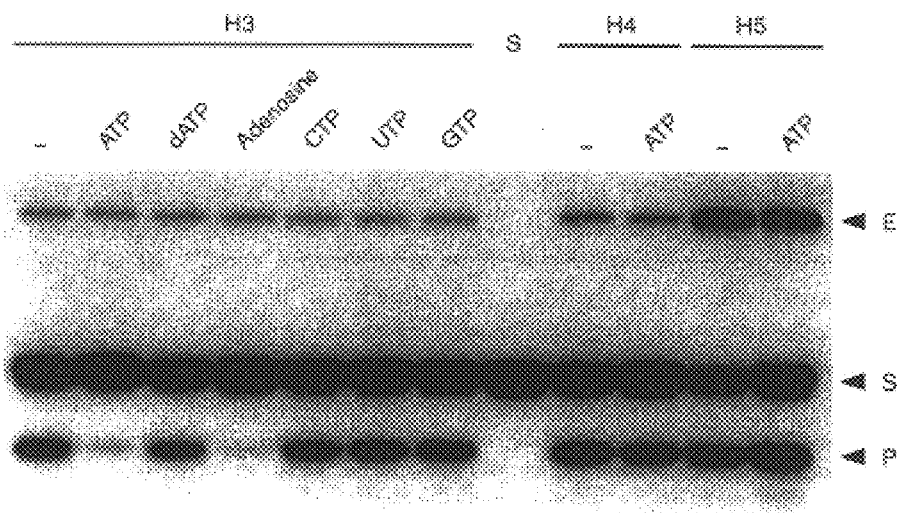

The RNA-cleavage activity of H3 is significantly reduced when incubated with 1 mM ATP (FIG. 6A). In contrast, ATP has no effect on the cleavage activity of H1 or H2. Moreover, inhibition is observed in the presence of adenosine, but not with dATP or the other ribonucleoside triphosphates (FIG. 2B). This inhibition is highly specific and is consistent with the observed binding specificity of the aptamer (35).

TABLE 1

Catalytic rates of various ribozyme constructs. Constructs denoted with * and †, contain either a functional ATP aptamer or a defective ATP aptamer, respectively.

| | | $k_{obs}$ (min$^{-1}$) | | |
|---|---|---|---|---|
| construct | stem II | none | ATP | dATP |
| H1 | A A<br>A G G C C<br>    \| \| \| \|<br>  A G C C G G | 0.58 | — | — |
| H2 | A A<br>A G G C C<br>    \| \| \| \|<br>  A G C C G G | 0.10 | — | — |
| H3* | C A A C<br>\| \| \| \|<br>G U U G | 0.054 | 0.00031 | 0.053 |
| H4† | C A A C<br>\| \| \| \|<br>G U U G | 0.042 | 0.061 | — |
| H5* | C A A G G C C<br>\| \| \| \| \| \| \|<br>G U U C C G G | 0.075 | 0.13 | — |
| H6* | C G U A U G C<br>\| • • \| • • \|<br>G U G C G U G | 0.022 | 0.12 | 0.027 |
| H7* | C G U G U G C<br>\| • • • • • \|<br>G U G U G U G | 0.0012 | 0.0098 | 0.0009 |

To investigate the mechanism of inhibition of H3 by ATP, two additional integrated constructs (FIG. 5) were designed.

H4 is identical to H3, but carries a G to C point mutation-that is expected to eliminate ATP binding by the aptamer domain (35). As expected, this mutation eliminates the inhibitory effect of ATP. The allosteric effect may be due to the proximity of the aptamer and hammerhead domains. Specifically, structural models of the hammerhead indicate a parallel orientation for stems I and II (32). In the uncomplexed state, the aptamer domain is likely to exist in a single or a set of conformational state(s) that allow catalysis to proceed unhindered. However, when complexed with ATP, this domain undergoes a conformational change that presumably causes steric interference between structures that are appended to stems I and II. H5 carries an additional three base pairs in helix II, to further separate the domains, and is not inhibited by ATP. This is consistent with an allosteric inhibition mechanism that involves conformational change and the mutually-exclusive formation of aptamer and ribozyme domains.

The inhibitory effect of ATP with H3 has been confirmed and quantitated by kinetic analysis. Ribozyme activity assays were conducted with trace amounts of substrate and excess ribozyme concentrations that significantly exceed $K_m$. Replicate $k_{obs}$ values obtained for H1 and H2 at 200, 400 and 800 nM ribozyme concentration under identical assay conditions differed by less that two fold, suggesting that for each construct, $k_{obs}$ values approach $V_{max}$. Reactions also contained 50 mM Tris-HCl (pH 7.5 at 23° C.) and 20 MM $MgCl_2$, and were incubated at 23° C. with concentrations of effector molecules and incubation times as noted for each experiments. Ribozyme and substrate were preincubated separately for ~10 min in reaction buffer and also with effector molecules when present, and reactions were initiated by combining preincubated mixtures. Assays with H8 were conducted in 50 mM HEPES (pH 7.3 at 23° C.), 500 mM NaCl and 10 mM $MgCl_2$. Catalytic rates ($k_{obs}$) were obtained by plotting the fraction of substrate cleaved versus time and establishing the slope of the curve that represents the initial velocity of the reaction by a least-squares fit to the data. Kinetic assays were analyzed by PAGE and were visualized and analyzed on a Molecular Dynamics Phosphorimager. When shorter effector-molecule preincubations are used, the catalytic burst was more prominent and when encountered, a post-burst slope was used in the calculations. Replicate experiments routinely gave $k_{obs}$ values that differed by less than 50% and the values reported are averages of two or more experiments. Equivalent rates were also obtained for duplicate ribozyme and substrate preparations.

The H3 ribozyme displays different cleavage rates, after a brief burst phase, with different concentrations of ATP (FIG. 7A), with the curve closely predicting the $K_D$ of the aptamer for its ligand. A plot of $k_{obs}$ versus ATP or dATP concentration (FIG. 7B) demonstrates that H3 undergoes ~170-fold reduction in catalytic rate with increasing concentrations of ATP, but is not inhibited by dATP.

Figure 8B:
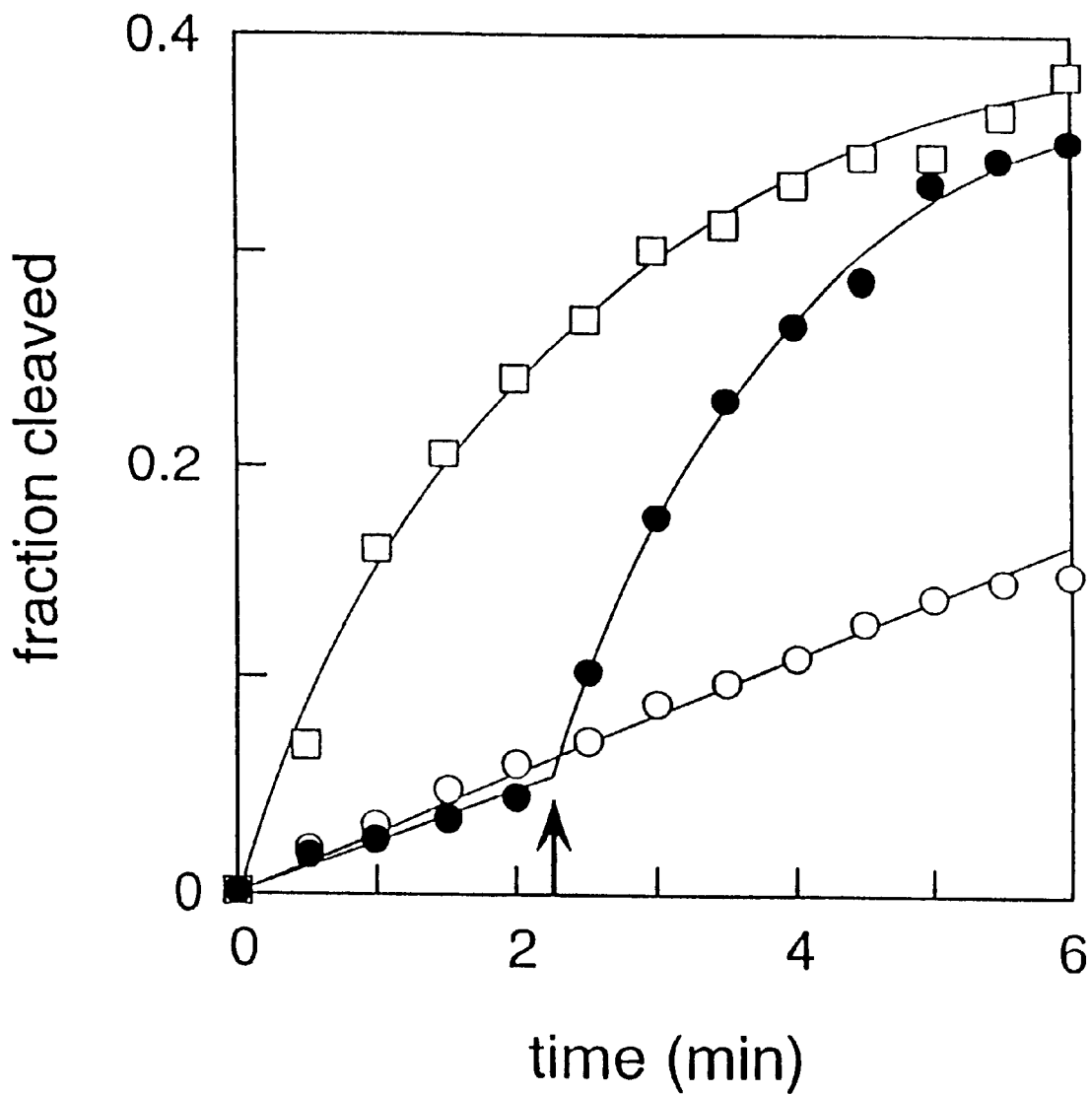
Figure 9A:
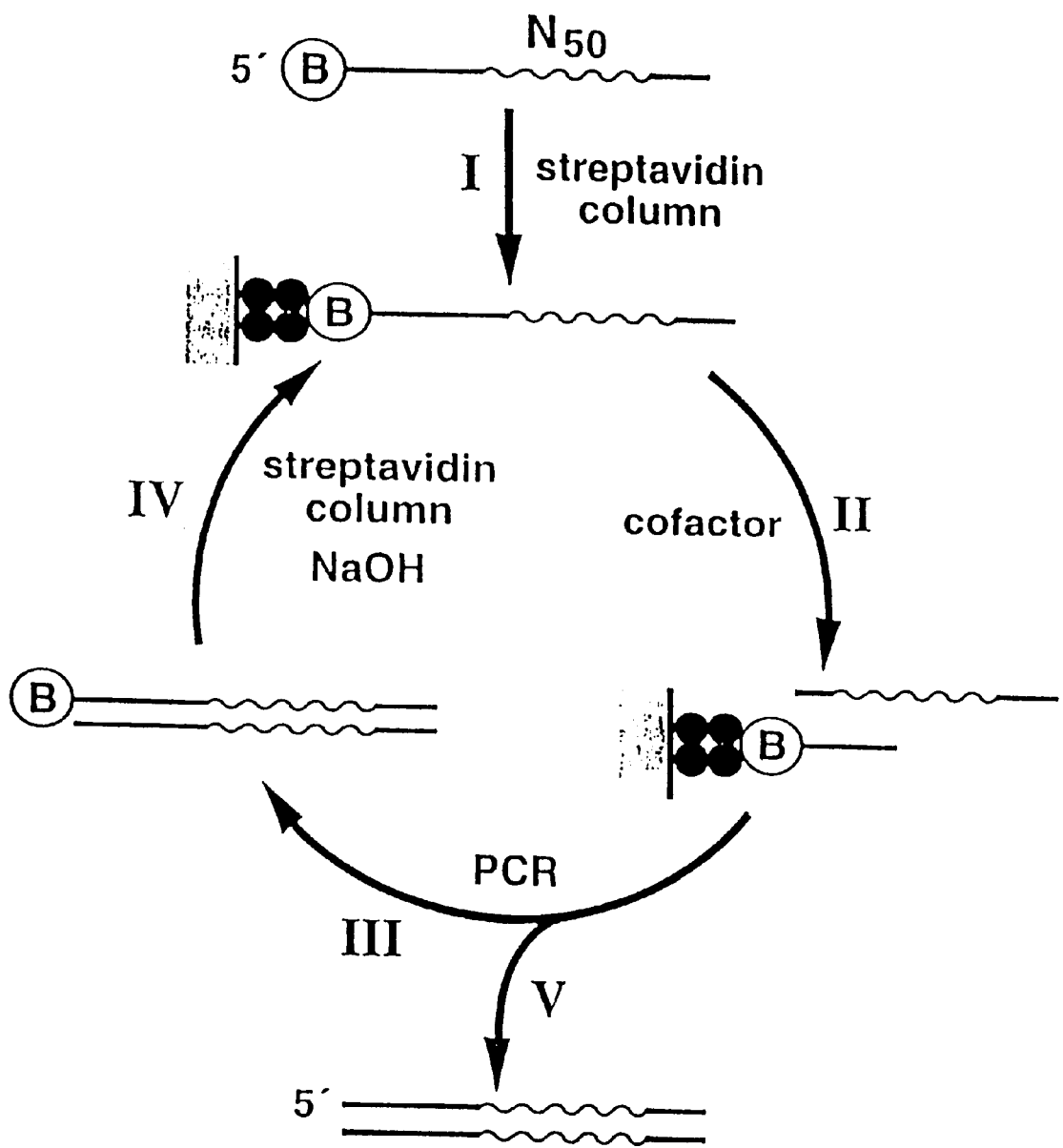
FIG. 9 shows in vitro selection of self-cleaving DNAs described in Example 2. In a a, (I) a pool of 5'-biotinylated DNAs is immobilized on a streptavidin matrix, washed to remove unbound DNAs, then (II) eluted under the desired reaction conditions to separate self-cleaving DNAs from those that are inactive. (III) Selected DNAs are amplified by the polymerase chain reaction (PCR) and (IV) the selection round is completed by immobilizing the resulting double-stranded DNAs on new matrix followed by removal of the nonbiotinylated strand by chemical denaturation. (V) The pool is prepared for further analysis by PCR amplification with non-biotinylated primers. Encircled B indicates 5' biotin. In b, the construct used for the initial round of selection contains a domain of 50 random-sequence nucleotides ($N_{50}$) flanked by 38 and 14 nucleotides of defined sequence. DNAs used in subsequent rounds carry an additional 26 nucleotides, as defined by primer 1. (SEQ ID NO: 7; primer 2 is SEQ ID NO: 8). Precursors that cleave within the overlined region retain sufficient 5' primer binding site for amplification and are expected to be favored during selection. In c, self-cleavage activity of the initial DNA pool (G0) and the pool isolated after seven rounds (G7) of selection. 5' $^{32}$P-labeled precursor DNA (Pre) was incubated in the presence (+) or absence (−) of 10 μM each of $Cu^{2+}$ and ascorbate, or in the absence of $Cu^{2+}$ or ascorbate (—$Cu^{2+}$ and -asc, respectively) for various times as indicated. M is 5' $^{32}$P-labeled primer 3 and Clv identifies cleavage products.
Figure 9B:
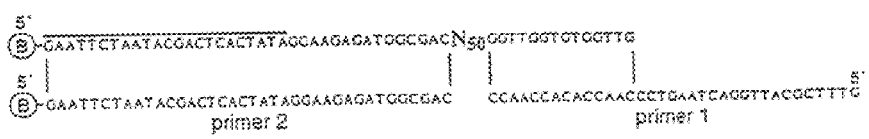
Figure 9C:
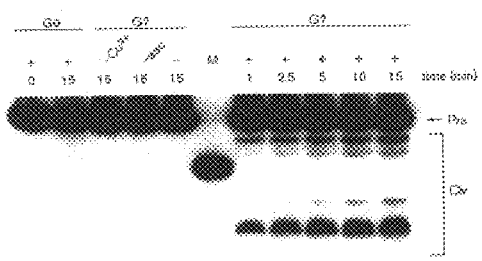

Whether ATP could also be made to function as a positive effector of ribozyme function was investigated by designing H6 and subsequently H7 (FIG. 8A), both which were found to display ATP-dependent allosteric induction. H6 is similar to H5, except that four Watson/Crick base-pairs in stem II are replaced with less-stable $G_oU$ mismatches. These changes are expected to significantly weaken stem II and result in diminished ribozyme activity. It was intended to exploit the fact that the G-C pair that begins stem II within the aptamer domain is not paired in the absence of ATP, but will form a stable pair when ATP is complexed (35), thereby increasing the overall stability of the stem and inducing catalytic activity. Indeed, a ~5-fold reduction in catalytic activity with H6 compared to H5 was found, yet ribozyme function could be specifically and fully recovered with ATP. The catalytic rate of H6 is also enhanced by ATP when added during the course of the reaction (FIG. 8B).

As with allosteric effectors of proteins, there is no true similarity between the effector molecule and the substrate of the ribozyme. Substrate and effector occupy different binding sites, yet conformational changes upon effector binding result in functional changes in the neighboring catalytic domain. The specificity of allosteric control of ribozymes can be exquisite, and in this example the ribozyme activity is sensitive to the difference of a single oxygen atom in the effector molecule.

With similar model studies, a palate of design options and strategic approaches that can be used to create ribozymes with controlled catalytic activity can be built. The principles used here (secondary binding sites, conformational changes, steric effects and structural stabilization) as well as others may be generally applicable and can be used to design additional allosteric ribozymes, or even allosteric deoxyribozymes (37). For example, an allosteric hammerhead (H8, FIG. 8A) that includes the theophylline aptamer described by Jenison, et al. (21) was designed. This construct displays a modest 3-fold reduction in ribozyme activity ($k_{obs}$ of 0.006 v. 0.002 $min^{-1}$) when theophylline is added to a final concentration of 100 $\mu$M. In addition, Sargueil, et al. (21) have suggested similar studies with the 'hairpin' self-cleaving ribozyme.

Example 2

The isolation by in vitro selection of two distinct classes of self-cleaving DNAs from a pool of random-sequence oligonucleotides are reported in this example. Individual catalysts from 'class I' require both $Cu^{2+}$ and ascorbate to mediate oxidative self-cleavage. Individual catalysts from class II were found to operate with copper as the sole cofactor. Further optimization of a class II individual by in vitro selection yielded new catalytic DNAs that facilitate $Cu^{2+}$-dependent self-cleavage with rate a enhancement that exceed 1 million fold relative to the uncatalyzed rate of DNA cleavage.

DNA is more susceptible to scission via depurination/$\beta$-elimination or via oxidative mechanisms than by hydrolysis (27). To begin a comprehensive search for artificial DNA-cleaving DNA enzymes, DNAs that facilitate self-cleavage by a redox-dependent mechanism were screened for. Cleavage of DNA by chelates of redox-active metals (e.g., $Fe^{3+}$, $Cu^{2+}$) in the presence of a reducing agent is expected to be a more facile alternative to DNA phosphoester hydrolysis due to the reactivity of hydroxyl radicals that are produced by reduction of $H_2O_2$ (i.e., Fenton reaction). Moreover, a variety of natural and artificial 'chemical nucleases' rely on similar cleavage mechanisms (38–39).

Beginning with a pool of $2 \times 10^{13}$ random-sequence DNAs (FIG. 13b), eight rounds of selection were carried out (5, 10) (see materials and methods section, below) for DNAs that self-cleave in the presence of $CuCl_2$ and ascorbate. The DNA pool that was isolated after seven rounds (G7 DNA) displays robust self-cleavage activity that requires both $Cu^{2+}$ and ascorbate (FIG. 13c). Trace amounts of non-specific DNA cleavage can be detected with $Cu^{2+}$ and ascorbate concentrations of 100 $\mu$M or above, but no cleavage of random-sequence (G0) DNA was detected under the final selection conditions (10 $\mu$M of each cofactor). In contrast, incubation of G7 DNA yields a number of distinct DNA cleavage products, suggesting that the pool contains multiple classes of DNAs that promote self-cleavage at unique sites.

Figure 10A:
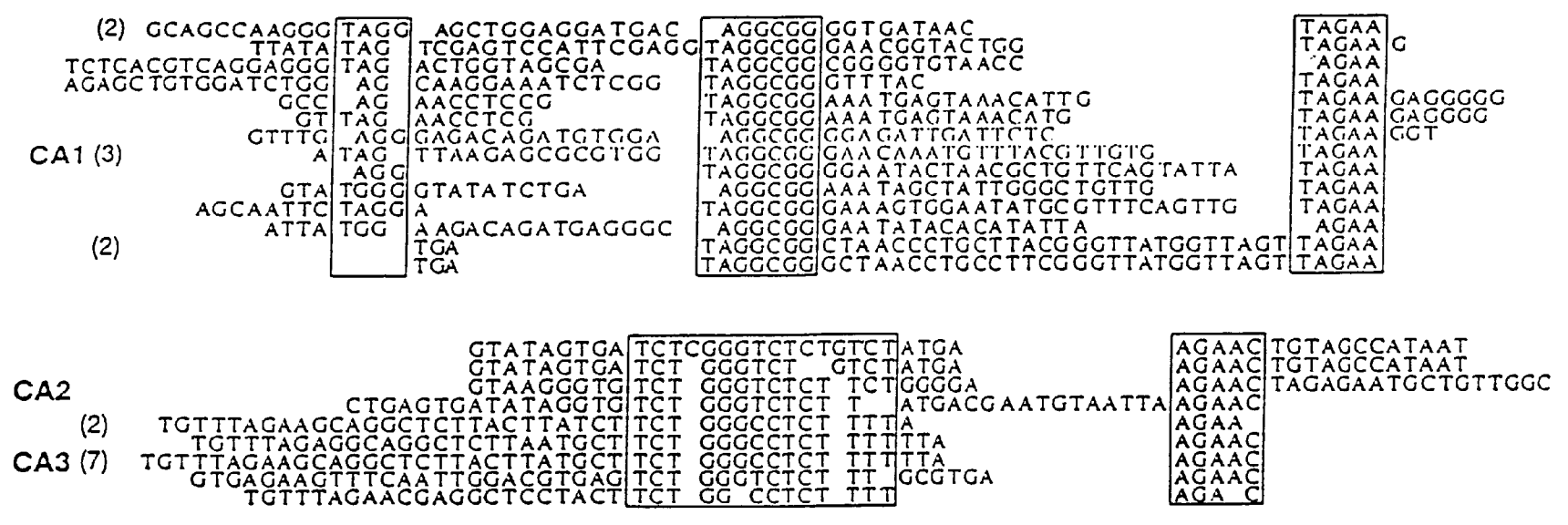
Figure 10B:
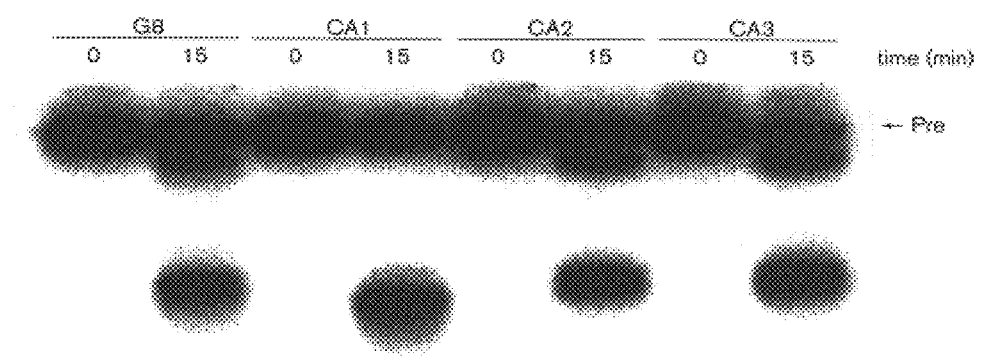
FIG. 10 shows sequence analysis and catalytic activity of individual G8 DNAs described in Example 2 (SEQ ID NOs: 9–31). In a, alignment of 34 sequences reveal the presence of two major classes of molecules that are characterized by sets of common sequences (boxed nucleotides). DNAs that were encountered more than once are identified by noting the number of occurrences in parentheses. In b, self-cleavage activity of ~5 nM 5' $^{32}$P-labeled precursor DNA from G8 DNA and from individuals CA1, CA2 and CA3 in the absence (−) or presence (+) of $Cu^{2+}$ and ascorbate (10 μM each) are shown.

Sequence analysis of individual DNAs from G8 reveals a diverse set of catalysts that were divided into two groups (FIG. 10a) based on sequence similarities. Cleavage assays from three representative DNAs (CA1, CA2 and CA3) confirm that two distinct classes of catalysts have been isolated (FIG. 10b). It was expected that the cleavage sites for the selected catalysts would reside exclusively within the first 2–3 nucleotides of the original construct (FIG. 13b). Cleavage in this region would result in release of the molecule from the solid matrix, yet the cleaved molecules would retain enough of the original primer-binding site to allow amplification by PCR. Cleavage elsewhere in a molecule would release a DNA fragment that has lost the 5'-terminal primer-binding site, and would be incapable of significant amplification 30 during PCR. Surprisingly, although CA1 promotes DNA cleavage within this expected region, CA2 and CA3 each cleave at a primary region (Clv 1) near the 5' terminus as expected, and at a distal region (Clv 2) that resides within the domain that was randomized in the original DNA pool. The Clv 1/Clv 2 product ratio of CA3 is approximately 2:1.

The distribution of cleavage products between the two sites in CA3 is expected to result in a significant disadvantage during the selection process. About 35% of CA3-like molecules cleave within the center of the molecule (and hence are probably not amplified), while only about 65% cleave at the expected site and can be perpetuated in the next round of selection via amplification by PCR. In contrast, 100% of the catalysts that cleave exclusively in the primer-binding region can be amplified, giving individuals from class I an apparent selective advantage. However, CA3-like catalysts were found to persist in additional rounds of in vitro selection and actually come to dominate the population by generation 13. The success of these catalysts can be understood, in part, by examining the catalytic rates of CA1 and CA3. The cleavage rate ($k_{obs}$) of 0.018 min$^-$ was obtained for CA1 under the final selection conditions, while cleavage at Clv 1 of CA3 occurs with a $k_{obs}$ of 0.14 min$^{-1}$. Despite a high frequency of miscleavage, class II catalysts more rapidly cleave at the correct site, giving CA3-like catalysts a distinct selective advantage over catalysts from class I.

Figure 11:
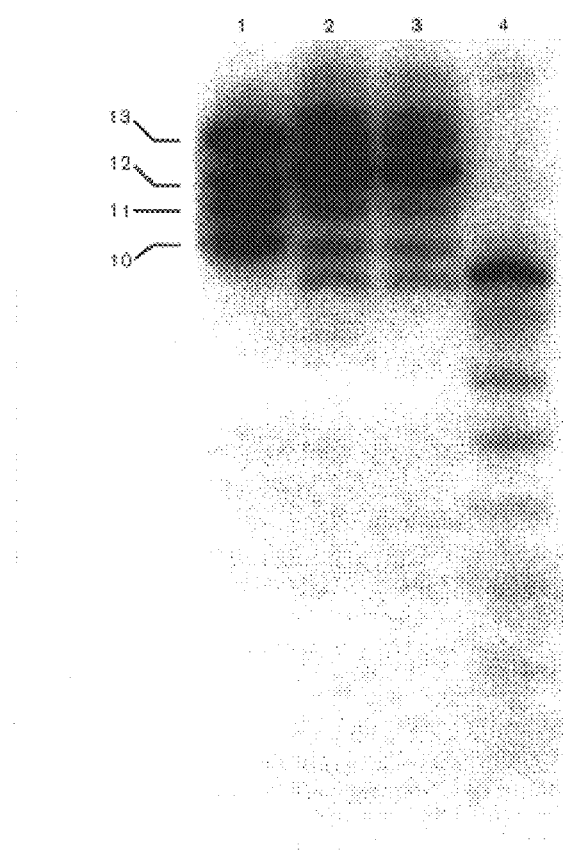
FIG. 11 depicts cleavage site analysis of CA3 (lane 2), an optimized variant (variant 1, FIG. 13b) of CA3 (lane 3) and CA1 (lane 4) described in Example 2. DNA size markers (lane 1) are 5' $^{32}$P-labeled DNAs of 10–13 nucleotides as indicated. The nucleotide sequence of these markers correspond to the 5' terminal constant region of the precursor.

Cleavage sites for both classes have been further localized by gel-mobility analysis of the 5' $^{32}$P-labeled self-cleavage products (FIG. 11). CA1 produces a major cleavage product with a gel mobility that corresponds to a 9-nucleotide fragment, and also yields a series of minor products that correspond to DNAs of 3 to 8 nucleotides. The cleavage site heterogeneity observed for CA1 is consistent with an oxidative cleavage mechanism that involves a diffusible hydroxyl radical. Typically, cleavage of nucleic acids by an oxidative cleaving agent occurs over a range of nucleotides, with a primary cleavage site flanked on each side by sites that are cleaved, with decreasing frequency. It has been suggested that the frequency of DNA cleavage is proportional to the inverse of the distance that separates the target phosphoester linkage and the generation site of the hydroxyl radical (18). However, the distribution of cleavage products formed by CA1 are indicative of a unique active site that permits localized DNA cleavage to occur only at nucleotides that immediately flank the 5' side of the major cleavage site.

Similarly, Clv 1 of CA3 consists of a series products that range in mobility from 9 to 14 nucleotides, with the major product corresponding to a 12-nucleotide DNA (FIG. 11). The major product formed upon DNA scission at Clv 2 corresponds to 70 nucleotides, with minor products corresponding to DNAs of 66–69 nucleotides. The most frequent site of cleavage at Clv 2 is located near position 34 (G) of the original random-sequence domain. Oxidative cleavage of DNA can proceed by a variety of pathways, each that produce distinct cleavage-product termini (22). Therefore, conformation of these cleavage sites must now proceed by conducting a more detailed analysis of the chemical structures of the reaction products.

Figure 12A:
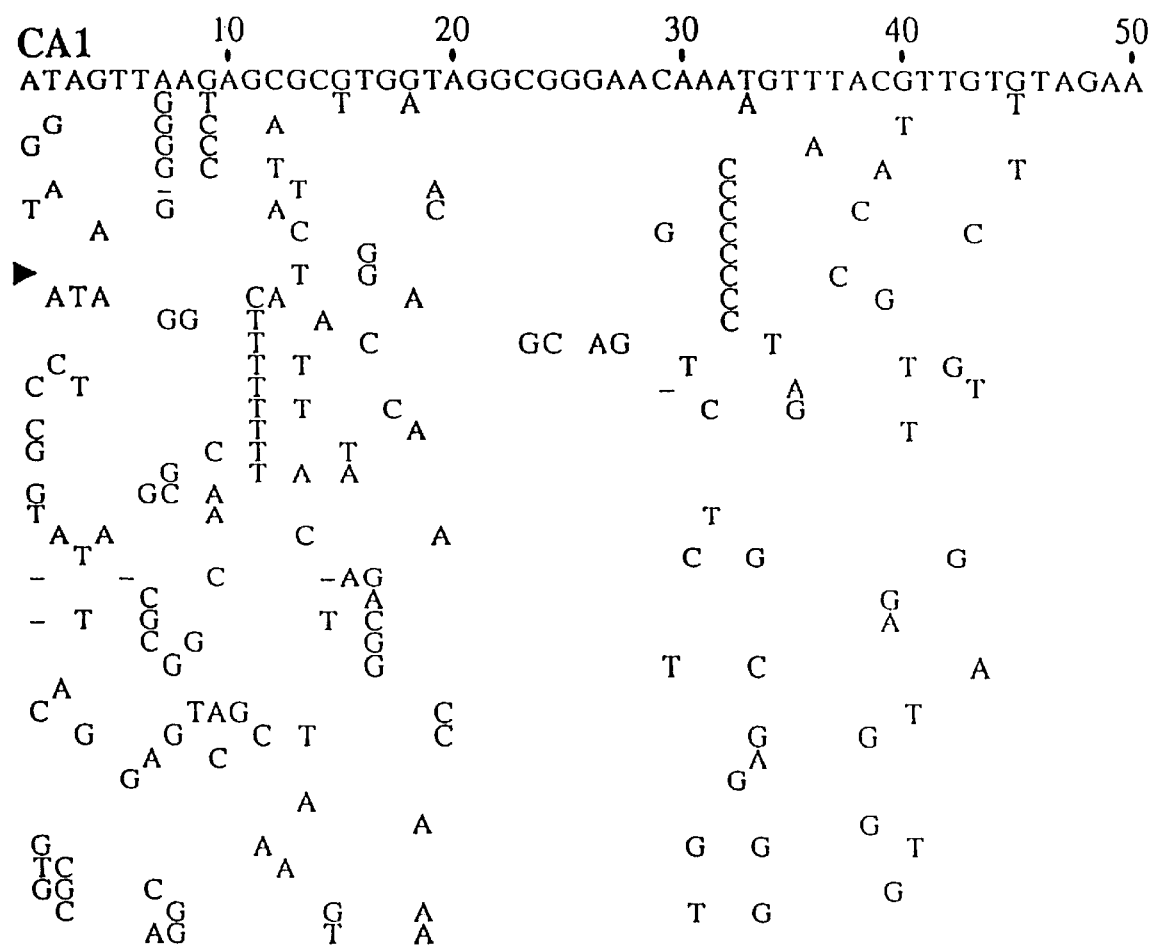
FIG. 12(a) shows an artificial phylogeny of CA1 (SEQ ID NO: 30) variants described in Example 2. The numbered sequence is wild-type CA1, and nucleotides of variants that differ from this sequence are aligned below. A dash indicates a deleted nucleotide. (b) Partial secondary-structure model for a variant of CA1 (arrowhead, SEQ ID NO: 32). Numbered nucleotides are derived from the region that was randomized in the starting pool. Asterisk indicates the primary cleavage site and the bar defines the region that undergoes detectable cleavage. Not detailed are nucleotides within the 3' primer binding site that are also required for catalytic activity.

To gain insight into the secondary structure of CA1, an artificial phylogeny (2) of functional CA1 sequence variants for comparative sequence analysis (47) were produced. The 50 nucleotides that corresponds to the original random-sequence. domain were mutagenized by preparing a synthetic DNA pool such that each wild-type nucleotide occurs with a probability of 0.85 and each remaining nucleotide occurs with a probability of 0.05. The resulting pool was subjected to five additional rounds of selection for activity in the presence of 10 µM each of Cu$^{2+}$ and ascorbate. Sequence alignment of 39 resulting clones (FIG. 12a) reveal two main regions (nucleotides 20–28 and 41–50) of strictly-conserved sequence interspersed with regions that tolerate variation. A total of 25 positions experienced two mutations or less. Other positions show sequence covariation, indicating that these nucleotides may make physical contact in the active conformation of the deoxyribozyme. For example, A32 and G40 frequently mutate to C or T, respectively. This suggests a preference for these bases to pair as C-G or A-T. Indeed, this inferred pairing occurs in a region (nucleotides 28–44) that has considerable base-pairing potential, consistent with the formation of a hairpin structure.

Figure 12B:
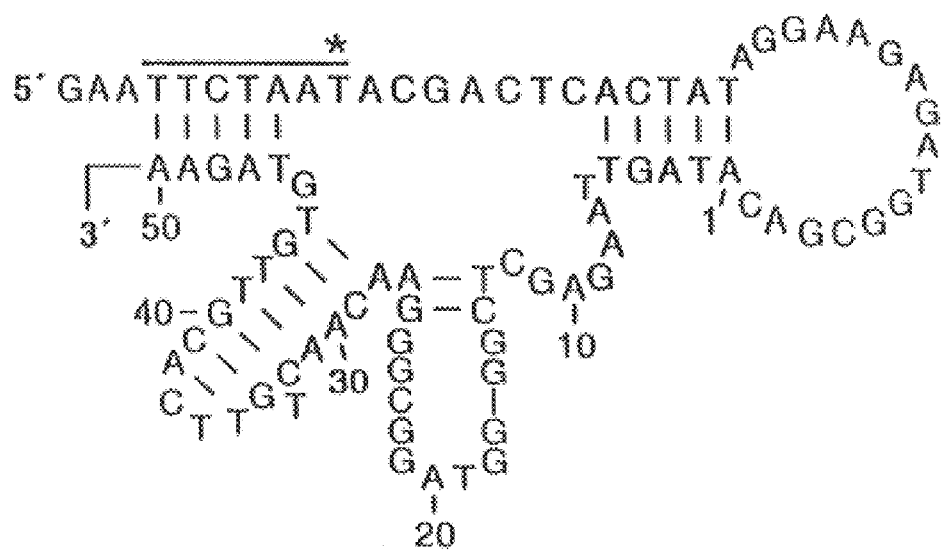

Using sequence data and truncation analyses, a partial secondary-structure model for CA1 was constructed (FIG. 12b). Both the 5'- and 3'-terminal nucleotides show significant base-pairing potential with the substrate domain of the molecule. The putative hairpin domain described above (nucleotides 28–44) is flanked by the conserved 3' terminus and by a highly-conserved region that is composed mainly of G residues. It was found that removal of an additional G-rich region that is located in the 3' primer binding site abolishes the catalytic activity of CA1. Extended stretches of G residues that form 'G-quartet' structures (46) have been identified in a number of other single-stranded DNAs (3,20, 26,48). The G-rich sequence in CA1 may also form a G-quartet, either independently or with other stretches of G residues that occur elsewhere in the primary structure of the catalyst.

Figure 13A:
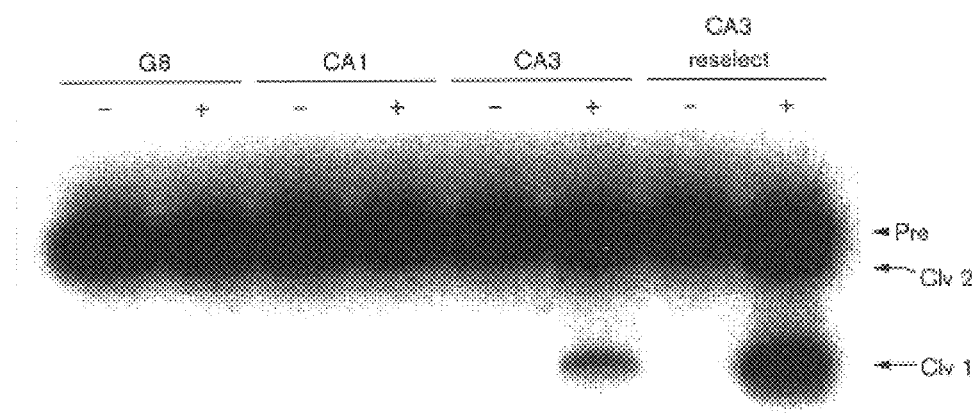
FIG. 13 shows a $Cu^{2+}$-dependent self-cleaving DNA described in Example 2. (a) Cleavage assay of G8 DNA, CA1 (SEQ ID NO: 30), CA3 (SEQ ID NO: 31) and the optimized population of CA3 variants was isolated after mutagenesis followed by five additional rounds of selection. (b) Sequence alignment of individual CA3 variants that have been optimized for catalytic function with $Cu^{2+}$. The numbered sequence is wild-type CA3, and nucleotides of variants that differ from this sequence are aligned below. A dash indicates a deleted nucleotide. Arrowheads identify CA3 variants 1–3 as denoted. Asterisk and bar indicate the major and minor Clv 2 cleavage sites, respectively.
Figure 13B:
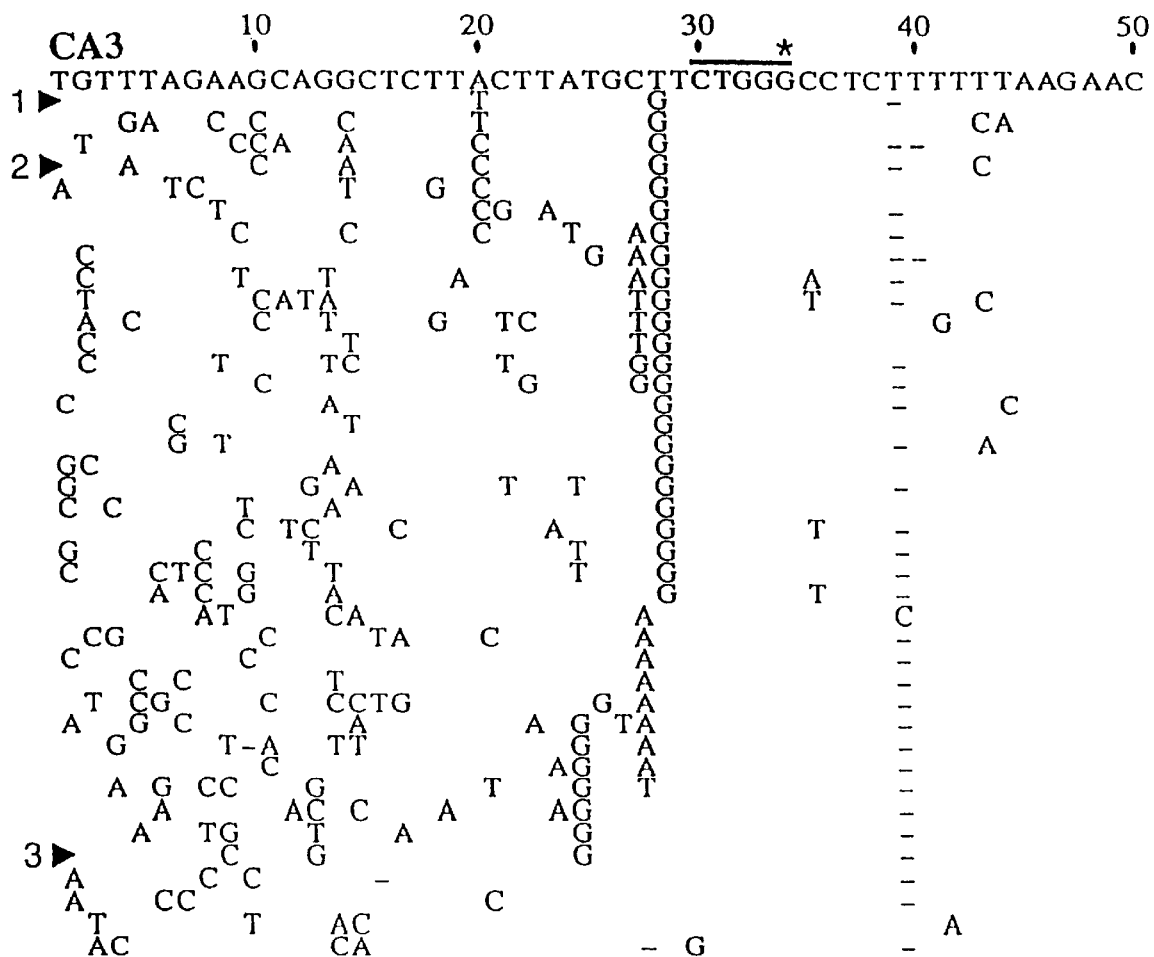

CA1 has no detectable activity in the absence of ascorbate, but surprisingly, both the G8 population DNA and CA3 display significant cleavage when only Cu$^{2+}$ is added (FIG. 13a). A $k_{obs}$=8×10$^{-4}$ min for Clv 1 was measured for CA3 in the presence of 10 µM Cu$^{2+}$. In vitro selection was employed to isolate CA3 variants with enhanced the Cu$^{2+}$-dependent activity of CA3. CA3 was mutagenized (see above) and subjected to five rounds of selection using 10 µM Cu$^{2+}$ as the sole cofactor. Sequence alignment of 40 resulting clones (FIG. 13b) reveal a single region of highly-conserved sequence, spanning nucleotides 15 to 50 of the original random-sequence domain. The base identity of 27 nucleotides within this region were found to vary in three or fewer individuals. The most notable exceptions to this sequence conservation are a T deletion between nucleotides 39 and 45, and a T to G mutation that occurs at nucleotide 28. In a related selection experiment, active variants of CA3 in which nucleotides 1 through 20 of the original random-sequence domain have been deleted were isolated.

The catalytic activity of the reselected CA3 pool improved by nearly 100-fold, with variant DNAs 1, 2 and 3 (FIG. 13b) displaying $k_{obs}$ values of 0.052 min$^{-1}$, 0.033 min$^{-1}$ and 0.043 min$^{-1}$, respectively. The uncatalyzed rate of DNA cleavage in the presence of Cu$^{2+}$ was assessed by incubating 5' $^{32}$P-labeled DNA oligomer (primer 3) under identical conditions. No Cu$^{2+}$-dependent cleavage of DNA was detected, even after a 2-week incubation at 23° C. The overall rate enhancement of the CA3 variants was estimated to be considerably greater than 10$^6$ fold compared to the uncatalyzed rate. Both CA3 and variant 1 likely proceed via the same DNA cleavage mechanism, as evident by their similar catalytic cleavage patterns (FIG. 11). A synthetic 87-nucleotide version of variant 1 that lacks the 3'-terminal primer-binding site remains active ($k_{obs}$=0.02 min$^{-1}$ for Clv 1, 10 µM Cu$^{2+}$), while an inhibitory effect is observed with 100 µM Cu$^{2+}$. In addition, the self-cleavage activity of this truncated DNA has a pH optimum of 7.5, with no specific monovalent-cation requirement. Sequential deletion of nucleotides from the 5' terminus of this DNA results in a progressive reduction in catalytic activity, with a 4-nucleotide deletion resulting in nearly complete loss of function.

The isolation of a variety of self-cleaving DNAs with Cu$^{2+}$/ascorbate-dependence is consistent with an earlier report (23) of site-specific cleavage of a single-stranded DNA under similar conditions. These results confirm that DNA is indeed capable of forming a variety of structures that promote chemical transformations. In addition, the catalytic rates for both classes of self-cleaving DNAs compare favorably to those attained by other deoxyribozymes and by natural and artificial ribozymes. The finding that DNA is also able to perform self-cleavage with Cu$^{2+}$ alone is unexpected, since the mechanism for the oxidative cleavage of DNA also requires a reducing agent such as ascorbate or a thiol compound (38,39).

A number of chemical nucleases have been prepared by others and examined for their potential as site-specific DNA-cleaving agents. For example, 1,10-phenanthroline and similar agents bind DNA, presumably via intercalation, and positions copper ions near the ribose-phosphate backbone where formation of a reactive oxygen derivative favors cleavage of the DNA chain (39). Alternatively, metal-binding ligands have been attached to oligonucleotide probes, in order to construct highly-specific DNA cleaving agents that recognize DNA by triple-helix formation (26). The catalytic DNAs described in this report likely replace the role of chemical nucleases by forming their own metal-binding pockets so as to promote region-specific self-cleavage. In fact, the addition of 1,10-phenanthroline to a catalytic assay of a synthetic class II DNA actually inhibits catalytic function. The optimal Cu$^{2+}$ concentration for the 87-nucleotide DNA is ~10 µM, with catalytic activity dropping significantly at both 1 and 100 µM Cu$^{2+}$. The inhibitory effect of 1,10-phenanthroline might be due to the reduction in concentration of free Cued upon formation of Cu$^{2+}$-phenanthroline complexes.

While not wishing to be bound to any theory, several different mechanisms for the oxidative cleavage of class II DNAs seem possible. For example, the class II DNAs may simply scavenge for trace amounts of copper and reducing agents that are present in the reaction buffer. Alternatively, these DNA molecules might make use of an internal chemical moiety as the initial electron donor. In each example, the catalytic DNAs could still cleave by an oxidative mechanism, but would at least appear to gain independence from an external source of reducing agent. The importance of H$_2$O$_2$ in oxidative processes can be examined with catalase, an enzyme that efficiently promotes the dismutation of H$_2$O$_2$ molecules to yield water and molecular oxygen. The catalytic activity of a representative DNA from class II is completely inhibited upon the addition of catalase, consistent with the notion that H$_2$O$_2$ is a necessary intermediate in an oxidative pathway for DNA cleavage. The catalytic rate of CA3 variants is greatly increased when incubated in the presence of added H$_2$O$_2$. For example, the 87-nucleotide DNA can be made to cleave quantitatively at Clv 1 ($k_{obs}$=1.5 min$^{-1}$) in the presence of 10 µM Cu$^{2+}$ and 35 mM H$_2$O$_2$.

It has not been determined whether trace amounts of H$_2$O$_2$ in water are used by the catalysts, or if the DNA can produce H$_2$O$_2$ in the absence of a reducing agent. It was found that preincubation of separate solutions of catalytic DNA in reaction buffer (minus Cu$^{2+}$) and of aqueous Cu$^{2+}$, followed by thermal denaturation of the catalase, results in full self-cleavage activity upon mixing of the two solutions. We also find that self-cleavage of the 87-nucleotide variant reaches a combined maximum (Clv 1+Clv 2) of ~70%, regardless of the concentration of catalytic DNA present in the reaction. Similarly, preincubation of a reaction mixture with excess unlabeled catalyst (1 µM) followed by the addition of a trace amount of identical 5' $^{32}$P-labeled catalysts produces normal yields of labeled-DNA cleavage products. Finally, addition of fresh reaction buffer to a previously-incubated reaction mixture does not promote further DNA cleavage, as might be expected if limiting amounts of reducing agent were responsible for activity.

Certain constructs of the self-splicing ribozyme of Tetrahymena have been shown to catalyze the cleavage of DNA via a transesterification mechanism (19,33), and the ribozyme from RNase P has been found to cleave DNA by hydrolysis (31). Such ribozymes might also be made to serve as therapeutic DNA-cleaving agents, analogous to the function of RNA-cleaving 'catalytic antisense' ribozymes (9). The secondary-structure model of CA1 (FIG. 12b) includes stretches of predicted base pairing both 5' and 3' to the primary cleavage site, suggesting that 'substrate' and 'enzyme' domains can be separated. Likewise, preliminary analysis of class II molecules reveals similar base complementation. It is expected that both class I and class II DNAs can be engineered to create catalytic DNAs that specifically cleave DNA substrates with multiple turn-over kinetics.

In summary, two distinct classes of DNAs that promote their own cleavage have been isolated. One class requires copper and catalyzes the oxidative cleavage of DNA with a rate in excess of 1 million fold. Extensive regions of both, classes of self-cleaving DNAs are important for the formation of catalytic structures, as implicated by sequence conservation found with selected individuals. These results support the view that DNA, despite the absence of ribose 2'-hydroxyl groups, has considerable potential to adopt higher-ordered structures with functions that are similar to ribozymes.

Materials and Methods

Oligonucleotides

All synthetic DNAs were prepared by automated chemical synthesis (Keck Biotechnology Resource Laboratory, Yale University). The starting pool is composed of DNAs that carry a 5'-terminal biotin moiety and a central domain of 50 random-sequence nucleotides. Primer 3 is an analogue of primer 1 (FIG. 13b) that contains a 3'-terminal ribonucleoside. Primer 4 is the nonbiotinylated version of primer 2 (FIG. 13b). Primer 5 is the 5'-biotinylated form of primer 1.

In Vitro Selection

A total of 40 pmoles of pool DNA in 40 µl buffer A (50 mm HEPES, pH 7.0 at 23° C., 0.5 M NaCl, 0.5 M KCl) was loaded on two streptavidin-matrix columns (Affinitip Strep20, Genosys Biotechnologies) and incubated for ~5 min. Unbound DNAs were subsequently removed from each column by pre-elution with 500 µl of buffer A, then by 500 µl 0.2 N NaOH, and the resulting matrix-bound DNAs were equilibrated with 500 µl buffer A. Catalytic DNAs were eluted with three successive 20-µl aliquots of buffer B (buffer A, 100 µM $CuCl_2$, 100 µM ascorbate) for rounds 1–3, or buffer C (buffer A, 10 µM $CuCl_2$, 10 µM ascorbate) for rounds 4–8. Eluate from each column was combined with 120 µl 4 mM EDTA and 40 pmoles each of primers 1 and 2. Selected DNAs and added primers were recovered by precipitation with ethanol and amplified by PCR a 200 µl reaction containing 0.05 µl-1 Taq polymerase, 50 mM KCl, 1.5 mM $MgCl_2$, 10 mM Tris-HCl (pH 8.3 at 23° C.), 0.01% gelatin, and 0.2 mM each dNTP for 25 cycles of 10 sec at 92° C., 10 sec at 50 ° C. and 30 sec at 72° C. The 5'-terminal region of each cleaved DNA, including the biotin moiety, was reintroduced at this stage. Subsequent rounds were performed by immobilizing 20 pmoles of pool DNA on a single streptavidin column and selected DNAs were amplified in a 100 µl reaction for 10 to 20 temperature cycles. Steps II–IV (FIG. 13) were repeated until the population displayed the desired catalytic activity, at which time the pool was PCR amplified with primers 1 and 3, cloned (Original TA Cloning Kit, Invitrogen) and sequenced (Sequenase 2.0 DNA Sequencing Kit, U. S. Biochemicals). Reselections with CA1 and CA3 were initiated with 20 pmoles synthetic DNA. This is expected to offer near comprehensive representation of all sequence variants with seven or fewer mutations relative to wild type.

Catalytic Assays

5'-$^{32}$P-labeled precursor DNA was prepared by PCR-amplifying double-stranded DNA populations or plasmid DNA using 5'-$^{32}$P-labeled primer 4 and either primer 5 or primer 3. The antisense strand is removed either by binding the biotinylated strand to a streptavidin matrix: (primer 5) or by alkaline cleavage of the RNA phosphodiester-containing strand, followed by PAGE purification (primer 3). DNA self-cleavage assays (~5 nM 5' $^{32}$P-labeled precursor DNA) were conducted at 23° C. in buffer A, with cofactors added as detailed for each experiment. For both in vitro selection and for assays, reaction buffers that contained ascorbate were prepared just prior to use. Self-cleavage assays conducted with catalase (bovine liver, Sigma) contained 50 mM HEPES (pH 7.0 at 23° C.), 50 mM NaCl, 10 µM $CuCl_2$, and 0.5 U/µl catalase, and were incubated at room temperature for 20 min. Catalase activity was destroyed by heating at 90° C. for 5 min. Products were separated by denaturing (8 M urea) polyacrylamide gel electrophoresis (PAGE) using a 10% gel and visualized by autoradiography or visualized and quantitated by PhosphorImager (Molecular Dynamics).

Cleavage Product Analysis

Primary cleavage sites for CA1 and CA3 were identified by incubating 5' $^{32}$P-labeled precursor DNA in buffer C and assessing the gel mobility of the 5'-terminal cleavage fragments by analysis using a denaturing 20% PAGE as compared to a series of 5' $^{32}$P-labeled synthetic DNAs that correspond in sequence to the 5' terminus of the precursor DNAs. Products resulting from sission at Clv 2 were analyzed by denaturing 6% PAGE.

Kinetic Analysis

Catalytic rates were obtained by plotting the fraction of precursor DNA cleaved versus time and establishing the slope of the curve that represents the initial velocity of the reaction as determined by a least-squares fit to the data. Kinetic assay s were conducted in buffer C or in buffer A plus 10 µM $CuCl_2$ as indicated for each experiment. Rates obtained from replicate experiments differed by less than two fold and the values reported are averages of at least two analyses.

Example 3

This example describes a DNA structure that can cleave single-stranded DNA substrates in the presence of ionic copper. This deoxyribozyme can self-cleave or it can operate as a bimolecular complex that simultaneously makes use of duplex and triplex interactions to bind and cleave separate DNA substrates. DNA strand scission proceeds with a $k_{obs}$ of 0.2 min$^{-1}$, a rate that is ~10$^{12}$-fold faster than the uncatalyzed rate of DNA phosphoester hydrolysis. The duplex and triplex recognition domains can be altered, making possible the targeted cleavage of single-stranded DNAs with different nucleotide sequences. Several small synthetic DNAs were made to function as simple 'restriction enzymes' for the site-specific cleavage of single-stranded DNA.

A Minimal $Cu^{2+}$-Dependent Self-cleaving DNA. In Example 2, a variety of self-cleaving DNAs were isolated by in vitro selection from a pool of random-sequence DNAs. Most individual DNAs that were isolated after eight rounds (G8) of selection conformed to two distinct classes, based on similarities of nucleotide sequence and DNA cleavage patterns. Although individual DNAs from both class I and class II require $Cu^{2+}$ and ascorbate for full activity, the G8 DNA population displays weak self-cleavage activity in the presence of $Cu^{2+}$ alone. A representative class II DNA termed CA3 was further optimized for ascorbate-independent activity by applying in vitro selection to a DNA pool that was composed of mutagenized CA3 individuals. The sequence data from this artificial phylogeny of DNAs indicates that as many as 27 nucleotides, most of them located near the 3' terminus of the molecule, are important for self-cleavage activity.

Beginning with the original G7 DNA population, an additional six rounds of in vitro selection was carried out for DNAs that self-cleave in the presence of 10 µM $Cu^{2+}$, without added reducing agent. Analysis of the G13 population of DNAs revealed robust self-cleavage activity, demonstrating that catalytic DNAs can promote efficient cleavage of DNA using only a divalent metal cofactor. The G13 population displays the same cleavage pattern that was observed with individual class II DNAs, indicating that class II-like DNAs dominate the final DNA pool.

Figure 14A:
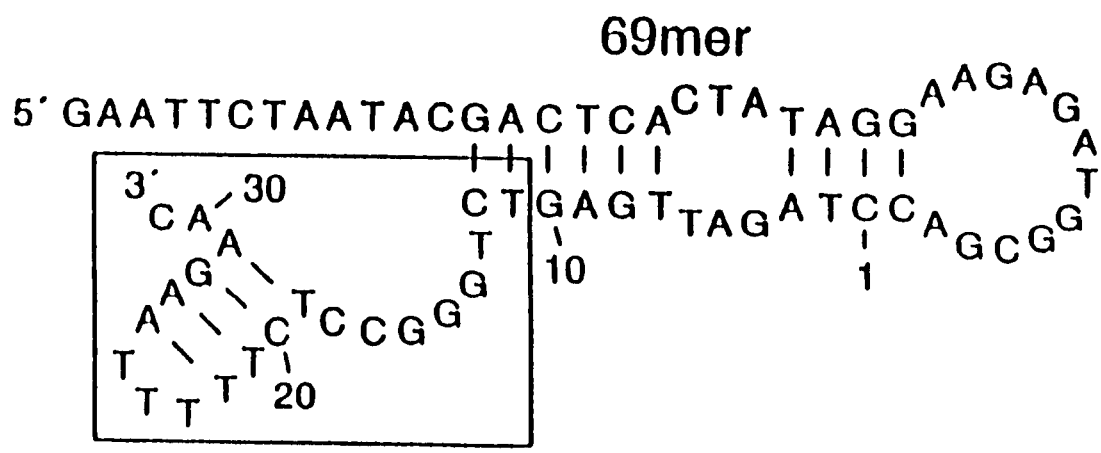
FIG. 14 shows the sequence and predicted secondary structures of minimized self-cleaving DNAs described in Example 3. (A) Sequence and secondary structure of a synthetic 69-nucleotide self-cleaving DNA that was isolated by in vitro selection (SEQ ID NO: 33). Numbers identify nucleotides that correspond to the 50-nucleotide random-sequence domain that was included in the original DNA pool (note that 19 bases of this domain have been deleted). The conserved nucleotides (11–31, boxed) are similar to those previously used to define this class of deoxyribozymes (Example 2). (B) A 46-nucleotide truncated version of class II DNAs that retains full activity (SEQ ID NO: 34). I and II designate stem-loop structures of the 46mer that are predicted by the structural folding program 'DNA mfold' (18, 19), and that were confirmed by subsequent mutational analysis (FIG. 15). The conserved core of the deoxyribozyme spans nucleotides 27–46 and the major site of DNA cleavage is designated by the arrowhead. Encircled nucleotides can be removed to create a bimolecular complex where nucleotides 1–18 constitute the 'substrate' subdomain, and nucleotides 22–46 constitute the 'catalyst' subdomain.

A total of 27 individual DNAs from G13 were sequenced and, without exception, each carried a 21-nucleotide sequence domain that largely conformed to the consensus sequence that was used previously to define class II self-cleaving DNAs. Although individuals that have a strictly conserved core (spanning nucleotides 11 to 31, FIG. 14A) dominate the G13 pool, two common variations from this consensus sequence include a C to T mutation at position 17 (6 of 28 individuals) or the presence of six successive T's instead of five in the region spanning nucleotides 21 to 25 (4 of 27 individuals). However, significant differences in nucleotide sequence were found to occur outside this conserved domain, indicating that large portions of the class II deoxyribozymes isolated may not be necessary for catalytic activity. Indeed, three individual DNAs were found to have undergone deletions of 16, 19, and 20 nucleotides within the 50-nucleotide domain that was randomized in the original starting pool. The predicted secondary structure for the 19-nucleotide deletion mutant (69mer DNA, FIG. 14A), obtained by the Zucker 'DNA mfold' program (33,50; the DNA mfold server can be accessed on the internet at www.ibc.wustl.edu/~zuker/dna/form1. cgi.), indicates the presence of three base-paired regions; two involve pairing between the original random-sequence domain and the 'substrate' domain, and one that involves putative base-pairing of nucleotides that lie within the conserved-sequence region. A synthetic DNA corresponding to the 69-mer depicted in FIG. 14A undergoes $Cu^{2+}$-dependent self-cleavage at two locations with a combined catalytic rate of approximately 0.3 $min^{-1}$ under the conditions used for in vitro selection (see Materials and Methods below for additional discussion on catalytic rates).

Figure 14B:
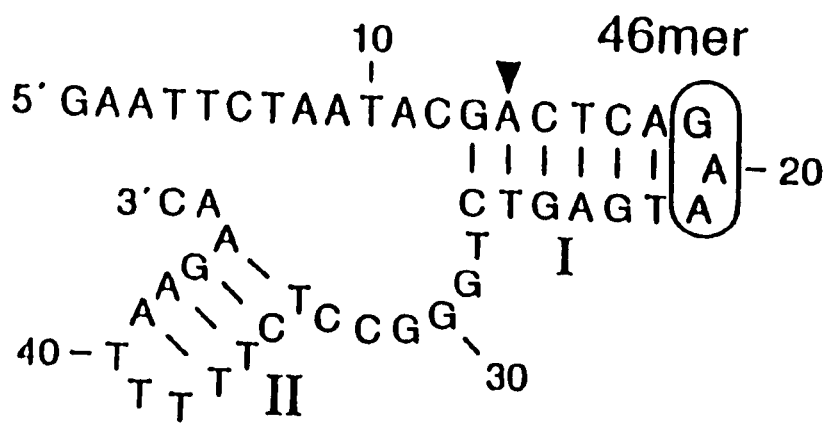

Whether the two pairing regions of the 69-mer that lie within the variable-sequence region could be replaced by a smaller stem-loop structure was tested by synthesizing a 46-mer DNA, in which 26 nucleotides of this imperfect hairpin were replaced by the trinucleotide loop GAA (FIG. 14B). As expected, the truncated '46mer' DNA retains full catalytic activity, thereby confirming that the deleted nucleotides are not essential for deoxyribozyme function. This 46-nucleotide deoxyribozyme is predicted to adopt a pistol-like secondary structure (FIG. 14B) composed of two base-paired structural elements (stems I and II) flanked by regions of single-stranded DNA. The primary site of DNA cleavage is located at position 14 which resides within one of the putative stem structures of the 46mer. The catalyst also promotes DNA cleavage within a region located apart from the main cleavage site (Example 2), as might be expected for a deoxyribozyme that makes use of an oxidative cleavage mechanism (22).

Figure 15A:
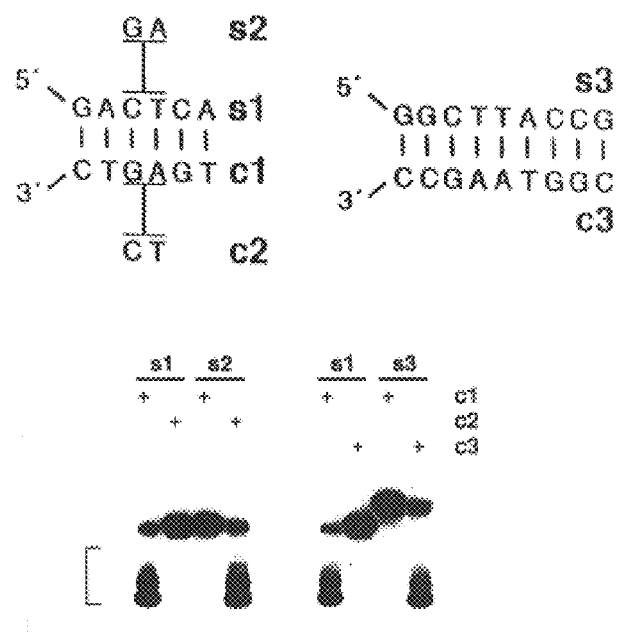
FIG. 15 shows a confirmation of stems I and II by mutational analysis described in Example 3. (A) Trace amounts of 5' $^{32}$P-labeled substrate DNAs (s1–s3) were incubated with 5 μM complementary or non-complementary catalyst DNAs (c1–c3) in reaction buffer A containing 10 μM $CuCl_2$ at 23° C. for 15 min. Reaction products were separated by denaturing 20% polyacrylamide gel electrophoresis (PAGE) and imaged by autoradiography. Bracket identifies the position of the substrate cleavage products. (B) Self-cleavage-activity of the original 46mer sequence compared to the activity of variant DNAs with base substitutions in stem II. Individual 46mer variants (100 μM 5' $^{32}$P-labeled precursor DNA) were incubated for the times indicated under reaction conditions as described above. Clv1 and Clv2 identify 5'-cleavage fragments produced upon precursor DNA (Pre) scission at the primary and secondary sites, respectively. Mutated positions are defined using the numbering system given in FIG. 14.

Bimolecular Deoxyribozyme Complexes: Substrate Recognition by Duplex and Triplex Formation. Separate 'substrate' and 'catalyst' DNAs can be created from the 46mer by eliminating the connecting loop of stem I (FIG. 14B). Active bimolecular complexes then can be reconstituted by combining independently prepared substrate and catalyst DNAs. Both the unimolecular 46mer and the bimolecular complexes examined cleave with identical rates, promoting primary-site cleavage with a $k_{obs}$ of approximately 0.2 $min^{-1}$. The importance of stem I was confirmed (FIG. 15A) by synthesizing different catalyst DNAs (c1, c2 and c3) and assessing their ability to cleave different substrate molecules (s1, s2 and s3). For example, c1 displays activity with its corresponding substrate (s1), but not when the non-complementary substrate DNAs s2 or s3 are substituted. Likewise, c2 and c3 only cleave their corresponding substrate DNAs s2 and s3, respectively. Extending stem I to create a more stable interaction was also found to confer greater binding affinity between substrate and catalyst oligonucleotides. These data indicate that base pairing interactions that constitute stem I are an essential determinant for catalyst/substrate recognition.

Figure 15B:
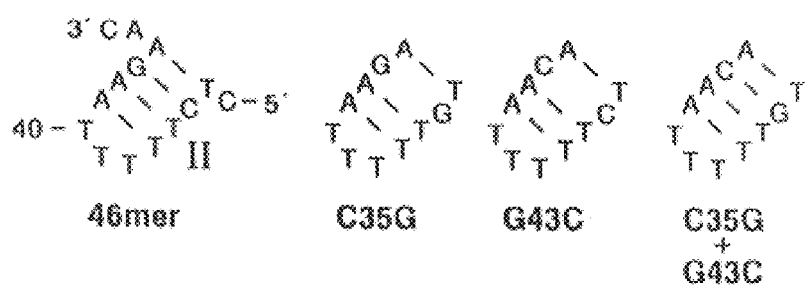

Stem II was examined by a similar approach using mutant versions of the 46mer self-cleaving DNA. A series of variant deoxyribozymes with one or two mutations included in the putative stem II structure were synthesized and assayed for catalytic activity (FIG. 15B); Disruption of the original C35-G43 base pair in stem II, either by mutation of C to G at position 35 or mutation of G to C at position 43, results in a substantial loss of activity. Cleavage activity is partially restored when these mutations are combined in the same molecule to produce a G35-C43 base pair. These results are consistent with the stem-loop structure modeled in FIG. 14. Additional support for the presence of stem II was found upon sequence analysis of the deoxyribozymes that are present in the original in vitro-selected pool of DNAs. A single self-cleaving DNA was found with a core sequence that differs significantly from that of the most frequently represented deoxyribozyme. Nucleotides 38–40 of the more common 46mer sequence are replaced in the variant deoxyribozyme with the nucleotides 5'-CTGGGG. This alternative sequence extends stem II by a single C-G base pair, consistent with the formation of the predicted stem-loop structure.

Although the existence of stem II is supported by the data derived from mutational analysis, the fact that total restoration of deoxyribozyme activity was not achieved with restoration of base complementation indicates that the identities of the base pairs in this structural element are important for maximal catalytic function. Moreover, it was found that mutation or deletion of nucleotides 1–7 of the 46mer result in a dramatic loss of DNA cleavage activity. It was recognized that nucleotides 4–7 within this essential region of the substrate form a polypyrimidine tract that is complementary to the paired sequence of stem II for the formation of a YR*Y DNA triple helix (14).

Figure 16:
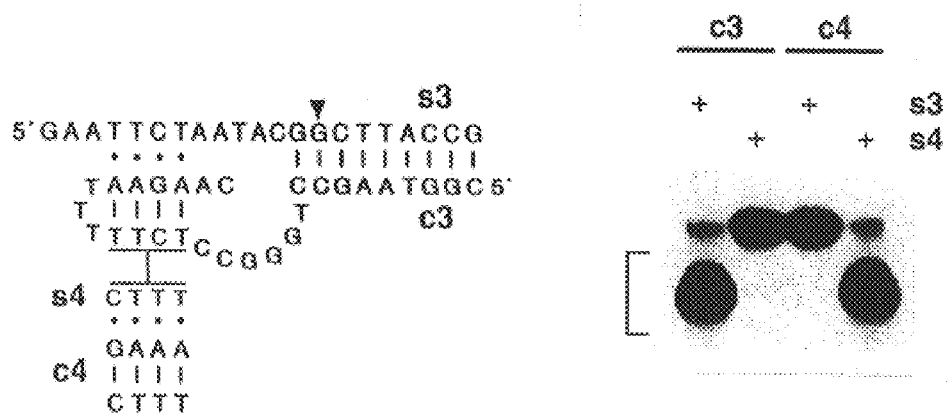
FIG. 16 identifies a triplex interaction between substrate and catalyst DNAs described in Example 3. A revised structural representation portrays a triple-helix interaction (dots) between the four base pairs of stem II and four consecutive pyrimidine residues near the 5' end of the substrate DNA. c4 and s4 represent sequence variants of c3 (SEQ ID NO: 36) and s3 (SEQ ID NO: 35) that retain base pairing within stem II, and that use an alternate sequence of base triples. DNA cleavage assays were conducted as described in FIG. 15A. Bracket identifies the position of the substrate cleavage products.

To examine the possibility of triplex formation in the active structure of the deoxyribozyme, we modified both the base pairing sequence of stem II (c4) and the sequence of the polypyrimidine tract of the substrate (s4) to alter the specificity, yet retain the potential for forming four contiguous base triples (FIG. 16). The c4 variant DNA cleaves its corresponding s4 DNA substrate, but shows no activity with a substrate that carries the original polypyrimidine sequence. It was found that even single mutations within stem II (e.g., FIG. 15B) or single mutations within the polypyrimidine tract cause significant reductions in catalytic activity. However, the introduction of six mutations in a manner that is consistent with triplex formation results in a variant (c4/s4) complex that displays full DNA cleavage activity. This is the first example of a catalytic polynucleotide, natural or artificial, that makes use of an extended triple helix for the formation of its active structure (43).

Figure 17A:
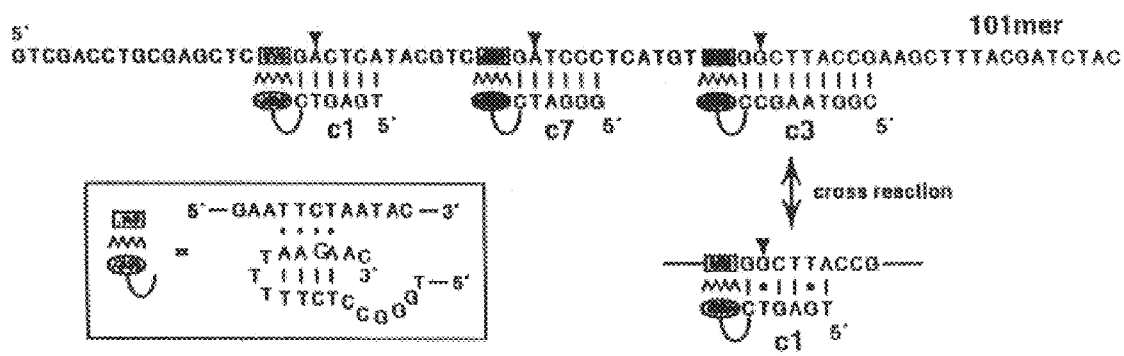
FIG. 17 shows targeted cleavage of DNA substrates using deoxyribozymes with engineered duplex and triplex recognition elements. (A) A 101-nucleotide DNA incorporating three different deoxyribozyme cleavage sites was prepared by automated chemical synthesis (SEQ ID NO: 37). Each cleavage site consists of an identical leader sequence (shaded boxes) followed by a stem I recognition element of unique sequence. The specific base complementation between the synthetic catalyst DNAs c1, c3 and c7 are also depicted. The catalytic core sequences and the leader sequence/stem II interactions for each site are identical (inset). Asterisks indicate G-T wobble pairs that allow cross reaction between c1 and the target for c3. Dots indicate base triple interactions. (B) Cleavage of the 101mer DNA by c1, c3, and c7 was examined by incubating trace amounts of 5' $^{32}$P-labeled substrate in reaction buffer containing 30 μM $CuCl_2$ at 23° C. for 20 min., either in the absence (−) or presence of 5 μM catalyst DNA as indicated. Reaction products were separated by denaturing 10% PAGE and visualized by autoradiography. (C). Similarly, a 100-nucleotide DNA was prepared that contained three identical stem I pairing regions (shaded boxes) preceded by eight successive pyrimidine nucleotides of unique sequence (SEQ ID NO: 38). Three synthetic deoxyribozymes (c9, c10, c11) that carry identical stem I paring elements (inset) and extended stem II subdomains of unique sequence, were designed to target the three cleavage sites exclusively through DNA triplex interactions. (D) Cleavage of 100mer DNA by c9, c10, and c11 was established as described in (B)
Figure 17B:
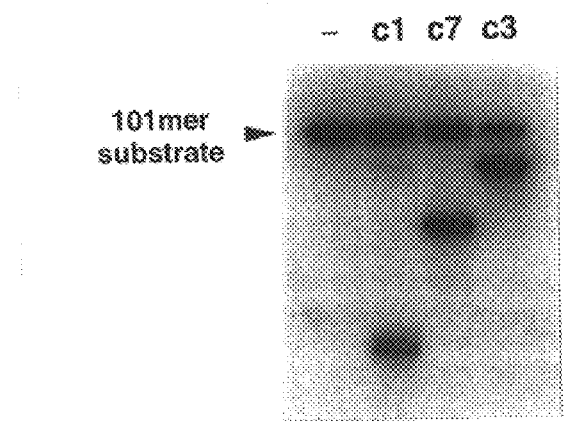

Targeted Cleavage of DNA 'Restriction Sites' with Deoxyribozymes. The results described above demonstrate that class II deoxyribozymes identify substrate DNAs by simultaneously utilizing two distinct recognition domains that are formed separately by stems I and II. These structures might be further exploited as recognition elements to engineer deoxyribozymes that selectively cleave DNAs at different target sites. To demonstrate this capability, a 10-nucleotide DNA that carries three identical leader sequences, each followed by different stem I recognition sequences was synthesized (FIG. 17A). Three catalyst DNAs (c1, c3 and c7) each were designed to be uniquely complementary to one of the three target sites. When incubated separately with 101mer substrate, DNAs c3 and c7 cleave exclusively at their corresponding target sites, while c1 cleaves at its intended site and also to a lesser extent at the c3 cleavage site (FIG. 17B). The cross reactivity observed with c1 can be explained by examining the base-pairing potential of stem I. Of the six nucleotides in the c1 recognition sequence, four can form standard base pairs, while the remaining two form G–T wobble pairs. The contribution of both duplex and triplex recognition elements presumably allows for detectable cleavage activity at this secondary location.

Figure 17C:
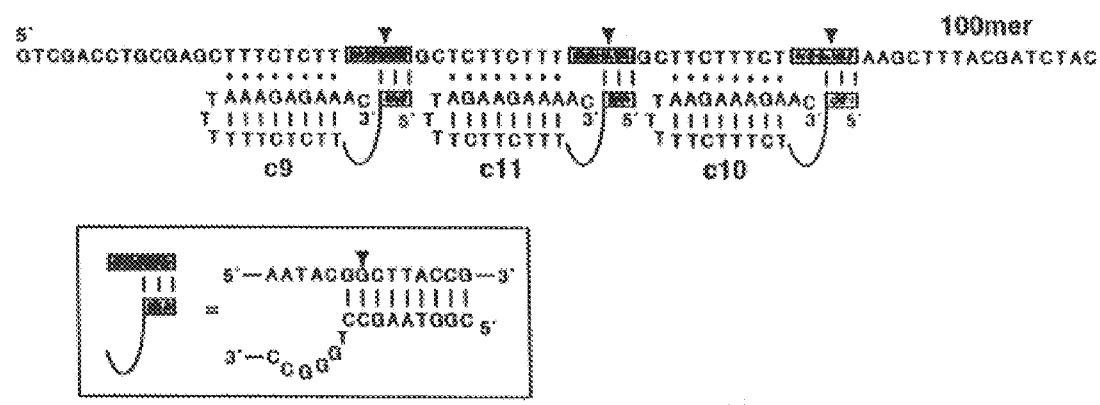

The triplex interaction that is defined by the base-pairing sequence of stem II can also be exploited to target specific DNA substrates. We designed three new catalyst DNAs (c9, c10 and c11) that carry identical stem I pairing subdomains, but that have expanded and unique stem II subdomains (FIG. 17C). When incubated separately with a 100-nucleotide DNA that carries three uniquely complementary polypyrimidine tracts, each catalyst DNA cleaves its corresponding target site with a rate that corresponds well with that found for the original self-cleaving DNA. In this example, substrate selectivity is determined almost entirely by triplex formation, despite the presence of identical and extensive base complementation (stem I) between catalyst and substrate molecules.

Although DNA cleavage catalyzed by the deoxyribozyme is focused within the substrate domain, substantial (~30%) cleavage occurs within the conserved core of the catalyst strand. This collateral damage causes inactivation of the deoxyribozyme and, as a result, super-stoichiometric amounts of catalyst DNA are needed to assure quantitative cleavage of DNA substrate. Cleavage of the substrate subdomain proceeds more rapidly than does cleavage within the catalytic core. In the presence of excess c1, s1 is cleaved at a rate of approximately 0.2 $min^{-1}$ (reaction buffer containing 30 $\mu$M $CuCl_2$), reaching a plateau of ~80% cleaved after 20 min. In contrast, cleavage of c1 in the presence of excess s1 proceeds more than 2-fold slower, consistent with our earlier-report that the ratio of self-cleavage localized in the substrate domain to self-cleavage in the catalytic core gives a ratio of ~2:1. It was established that, barring inactivation by miscleavage, the catalyst strand can undergo multiple turnover.

Cleaving Double-stranded DNA by Thermocycling. Class II catalyst DNAs are not able to cleave target DNAs when they reside within a duplex. The catalyst DNA, with its short recognition sequence, presumably cannot displace the longer and more tightly-bound complementary strand of the target in order to gain access to the cleavage site. It was found that an effective means for specific cleavage of one strand of an extended DNA duplex makes use of repetitive cycles of thermal denaturation and reannealing. For example, c3 remains inactive against a double-stranded DNA target in the absence of thermal cycling, but efficiently cleaves the same DNA substrate upon repeated heating and cooling cycles. Cleavage of the radiolabeled target is quantitative after 6 thermal cycles. DNA cleavage by class II DNAs occurs within the base-pairing region corresponding to stem I, presumably when this region is in double-helical form. This, coupled with the observation of substrate recognition by triplex formation, suggests that different DNA enzymes might be engineered to cleave duplex DNA substrates without the need for thermal denaturation. Such deoxyribozyme activity would be similar to that performed by a number of triplex-forming oligonucleotides that have been engineered to bind and cleave duplex DNA using a chemically-tethered metal complex such as Fe-EDTA (24–27).

Conclusions. In its unimolecular arrangement, the class II deoxyribozyme could be used to confer the capacity for self-destruction to an otherwise stable DNA construct. In its bimolecular form, the deoxyribozyme can act as an artificial restriction enzyme for single-stranded DNA, whereas protein-based nucleases that cleave non-duplex DNA do not demonstrate significant sequence specificity. It is likely that Ymaximal discrimination by class II catalysts between closely related target sequences can be achieved through careful design of the duplex and triplex recognition domains. This is expected to eliminate the cross reactivity that was observed here. Although the role of most nucleotides within the substrate domain are involved in substrate recognition, the importance of each nucleotide within the leader sequence has yet to be fully delineated. However, guided by the basic rules of duplex and triplex formation, one w3can now engineer highly-specific deoxyribozymes that can catalyze the cleavage of single-stranded DNA at defined locations along a polynucleotide chain.

Materials and Methods

Oligonucleotides

Synthetic DNAs were prepared by automated chemical synthesis (Keck Biotechnology Resource Laboratory, Yale University), and were purified by denaturing (8 M urea) polyacrylamide gel electrophoresis (PAGE) prior to use. Double-stranded 101mer DNA was prepared by the polymerase chain reaction (PCR) as described in Example 2 using the primer DNAs 5' $^{32}$P-GTCGACCTGCGAGCTCGA, (SEQ ID NO: 51) 5' GTA-GATCGTAAAGCTTCG (SEQ ID NO: 52) and the 101mer DNA oligomer (FIG. 17A) as template.

In Vitro Selection

Optimization of class II self-cleaving DNAs was achieved by in vitro selection essentially as described In Example 2 using a reaction mixture for DNA cleavage composed of 50 mM HEPES (pH 7.0 at 23° C.), 0.5 M NaCl, 0.5 M KCl (buffer A), and that included 10 $\mu$M $CuCl_2$. The selection process was initiated with 20 pmoles G7 PCR DNA in which the 5' terminus of each catalyst strand carried a biotin moiety, thereby allowing DNA from this and subsequent generations to be immobilized on a streptavidin-derivatized chromatographic matrix. Reaction time was 15 min. for immobilized DNA from G8–G10 and 12, 7 and 5 min. for the G11–G13 DNA populations, respectively. Individual self-cleaving DNAs from G13 were analyzed by cloning (Original TA Cloning Kit, Invitrogen) and sequencing (Sequenase 2.0 DNA Sequencing Kit, U.S. Biochemicals).

DNA Cleavage Assays

To assess the DNA cleavage activity of self-cleaving-molecules, radio-labeled precursor DNA was prepared by enzymatically tagging the 5' terminus of synthetic DNAs in a reaction containing 25 mM CHES (pH 9.0 at 23° C.), 5 mM $MgCl_2$, 3 mM DTT, 1 $\mu$M DNA, 1.2 $\mu$M ($\gamma$-$^{32}$P)-ATP (~130 $\mu$Ci), and 1 U/$\mu$L T4 polynucleotide kinase, which was incubated at 37° C. for 1 hr. The resulting 5' $^{32}$P-labeled DNA was isolated by denaturing PAGE and recovered from the gel matrix by crush-soaking in 10 mM Tris-HCl (pH 7.5 at 23° C.), 0.2 M NaCl, and 1 mM EDTA. The recovered DNA was concentrated by precipitation with ethanol and resuspended in deionized water (Milli-Q, Millipore). Self-cleavage assays using trace amounts of radiolabeled precursor DNA (100 $\mu$M) were conducted at 23° C. in buffer A containing $CuCl_2$ as indicated for each experiment. Examinations of the DNA cleavage activity of bimolecular complexes were conducted under similar conditions using trace amounts of 5' $^{32}$P-labeled 'substrate' DNA. Cleavage products were separated by denaturing PAGE, imaged by autoradiography or by PhosphorImager (Molecular Dynamics) and product yields were determined by quantitation (ImageQuant) of the corresponding precursor and product bands.

Kinetic Analyses

Catalytic rates were estimated by plotting the fraction of precursor or substrate DNA cleaved versus time and establishing the slope of the curve that represents the initial velocity of the reaction as determined by a least-squares fit to the data. Upon close examination, DNA cleavage in-both the substrate and enzyme domains displayed a brief lag phase that complicates the determination of the initial cleavage rate. In order to avoid the lag phase, the initial slope was calculated only using data collected after the reaction had proceeded for 1 min. Rates obtained from replicate experiments differed by less than 50% and the values reported are averages of at least three analyses.

Example 4

The in vitro selection of a catalytic DNA that uses histidine as the active component for an RNA cleavage reaction is described in this example. An optimized deoxyribozyme only binds to L-histidine or to several closely-related analogues and subsequently catalyzes RNA phosphoester cleavage with a rate enhancement of ~10-million fold over the uncatalyzed rate. While not wishing to be bound to any theory, the DNA-histidine complex apparently performs a reaction that is analogous to the first step of the catalytic mechanism of RNase A, in which the imidazole group of histidine acts as a general base catalyst.

The class of deoxyribozymes that catalyze the cleavage of an RNA phosphoester bond using the amino acid histidine as a .cofactor described herein is depicted in FIG. 18a. To assure that metal-dependent deoxyribozymes were not recovered from the random-sequence pool of DNAs, the divalent metal-chelating agent ethylenedimainetetraacetic acid (EDTA) was included in a reaction mixture that was buffered with 50 mM histidine (pH 7.5). After 11 rounds of selective amplification, the DNA pool displayed RNA phosphoester-cleaving activity, both under in vitro selection conditions, and in a reaction buffer containing HEPES (50 mM, pH 7.5) in place of histidine. Individual molecules cloned from the final DNA pool were grouped into one of four sequence classes (FIG. 19b), and representative clones were tested for catalytic activity. Only class II DNAs demonstrate complete dependence on histidine while the remaining classes appear to operate independently of any metal ion or small organic cofactor.

The catalytic rate for the original class II deoxyribozyme was ~1000-fold slower ($k_{obs}=1.5\times10^{-1}$ min$^{-1}$) than most natural self-cleaving ribozymes (44). As a result, further optimization of catalytic activity was sought in order to provide an artificial phylogeny of variant catalysts for comparative sequence analysis. A new DNA pool was prepared based on the sequence of class II deoxyribozymes, such that the 39 nucleotides corresponding to the original random-sequence domain were mutagenized with a degeneracy of 0.21 (6). Beginning with a mutagenized pool that sampled all possible variant DNAs with seven or fewer mutations relative to the original class II sequence, parallel reselection was conducted using reaction solutions buffered with either 50 mM histidine, or with 5 mM histidine and 50 mM HEPES. Individual DNAs isolated from the populations resulting from five rounds of reselection are more active than the original class II deoxyribozyme, and show specific patterns of conserved sequences and mutation acquisition (FIG. 19a).

It was speculated that engineered pairing element i included in the original DNA construct (FIG. 18a) was being utilized by class II deoxyribozymes. In contrast, it was recognized that a conserved-sequence domain near the 3' end of the core (FIG. 19a, nucleotides 32–36) was identical to pairing element ii. Considering these observations, individual deoxyribozymes HD1 and HD2 were designed to operate as separate substrate and enzyme domains (FIG. 19b). Specificity for the substrate oligonucleotide is defined by the Watson/Crick base complementation between the substrate and the two pairing arms of the enzyme domain. Class II deoxyribozymes have an absolute requirement for histidine as show by the activity of the bimolecular HD1 construct to 'caged' histidine delivered in the form of dipeptides, and to free amino acids that were liberated from each dipeptide by acid hydrolysis (FIG. 16a). In addition, HD1 accepts L-, but not D-histidine as a cofactor. However, samples of D-histidine become active upon treatment with HCl in accordance with the accelerated rate of interconversion between the two isomeric forms in acidic conditions (11).

A larger panel of histidine analogues were examined (FIG. 16b) in order to more carefully examine the chemical groups of histidine that are important for catalytic activity and to rule out the possibility that catalysis might be due to a contamination of a metal ion cofactor. HD1 discriminates against a variety of histidine analogues, but shows full activity with the methyl ester of L-histidine (FIG. 16c). Both the 1-methyl- and 3-methyl-L-histidine analogues do not support HD1 activity, indicating that the imidazole ring of histidine is important for deoxyribozyme function. As expected, HD2 has a similar pattern of cofactor discrimination (Table 2). Both catalysts show stereospecific recognition of histidine, and make use of interactions with the α-amino group, with both carboxyl oxygens, and with the imidazole group in order to attain maximize cofactor binding. Although a number of analogues cannot support deoxyribozyme activity, no compounds function as competitive inhibitors, indicating that their inactivity is due to the failure to bind the deoxyribozyme.

TABLE 2

Relative $k_{obs}$ values for HD2 in the presence of 25 mM L-histidine and various analogues ($k_{obs}$ for L-histidine = 0.11 min$^{-1}$).

| cofactor | relative $k_{obs}$ | fold discrimination |
| --- | --- | --- |
| L-histidine | 1 | — |
| L-histidine methyl ester | 0.93 | 1.1 |
| L-histidine benzyl ester | 0.76 | 1.3 |
| α-methyl-DL-histidine | 0.041 | 24 |
| histidinamide | 0.025 | 40 |
| glycyl-histidine | 0.006 | 170 |
| histidinol | 0.003 | 330 |
| 3-methyl-L-histidine | 0.002 | 500 |
| D-histidine | 0.001 | 1000 |
| 1-methyl-L-histidine | $<10^{-3}$ | >1000 |

The rate constant for HD2-promoted catalysis ($k_{obs}$ of 0.2 min$^{-1}$, 50 mM histidine) is similar to that of natural self-cleaving ribozymes and corresponds to a rate enhancement of 10 million fold over the uncatalyzed reaction ($k_{obs}<10^{-8}$ min$^{-1}$ under in vitro selection conditions). The dependence of the rate constant on histidine concentration is characteristic of the presence of a saturable binding site for histidine, although neither HD2 nor HD1 reach saturation even at 100 mM concentration of cofactor. The established specificity for particular cofactors, however, indicates that both catalysts do indeed form a histidine binding site. HD2 demonstrates greater activity with lower histidine concentrations, perhaps reflecting a greater binding affinity for histidine as would be expected due to its isolation from a low-histidine selection regiment.

Figure 21B:
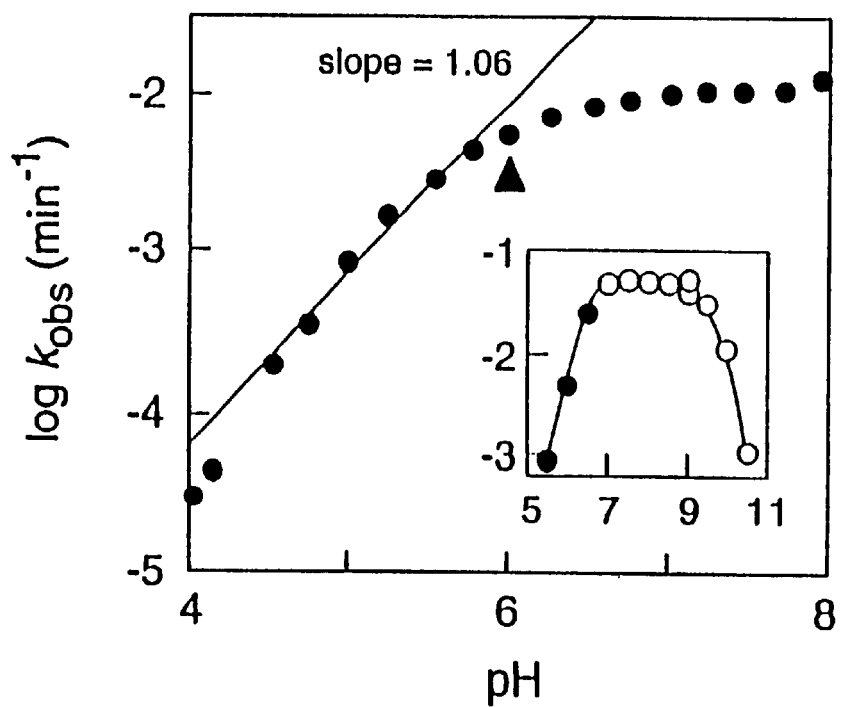

The pH-dependent activity profile for HD2 also implicates histidine as an integral component of the catalytic process (FIG. 21b). The rate constant of HD2 is entirely independent of pH between the values 7 and 9. However, the activity of this enzyme drops precipitously at pH values that lie outside this optimum range. Most revealing is the response of HD2 to low pH conditions. The $k_{obs}$ values increase linearly with increasing pH between pH 4.5 and 5.5, giving a slope of approximately 1. This result is expected if the protonation state of a single functional group determined the catalytic rate. Moreover, a rate constant that is half the maximum value is obtained at pH 6, where this chemical group will be half deprotonated. This value corresponds precisely with the $pK_a$ for the imidazole group of free histidine. Taken together, these results are consistent with a mechanism whereby the imidazole group serves as a general base catalyst for the deprotonation of the 2'-hydroxyl group, thereby activating the oxygen for nucleophilic attack on the neighboring phosphorus atom.

The loss of catalytic activity at higher pH values is not expected to be due to the protonation state of histidine, unless the $pK_a$ of the imidazole group of a putative second histidine cofactor is dramatically shifted from its normal value. The β-amino group of histidine, which has a $pK_a$ of greater than 9, conceivably could be involved in catalysis as well. However, it is expected to find a loss of activity with pH values in excess of 9 or less than 4.5 due to the significant level of deprotonation of T and G residues or protonation of C and A residues, respectively.

Histidine was chosen as a candidate cofactor because of the potential for the imidazole side chain to function in both general acid and general base catalysis near neutral pH. This property is neither inherent to the four standard nucleotides of RNA nor to the remaining natural amino acids. As a consequence, histidine is one of the most-frequently used amino acids in the active sites of protein enzymes. For example, two active-site histidines are essential for the function of ribonuclease A from bovine pancreas, where both of these capacities are used to accelerate RNA cleavage. Although RNase A has long served as a model for the-study of enzyme action, the specific roles that each active-site reside play in the catalytic process are still vigorously debated (31). The classical view holds that the histidine at position 12 acts as a general base for the deprotonation of the 2' hydroxyl, while the histidine at position 119 acts as a general acid and protonates the 5' oxyanion leaving group. Breslow and others (25,47) have proposed that the role for histidine 119 instead may be to protonate the phosphorane intermediate, thereby implicating general acid catalysis by the imidazole group as a priority step during the catalytic process. The data described herein indicate that the histidine cofactor for class II deoxyribozymes is not involved in a protonation step, but is functioning exclusively as a general base catalyst.

In comparison to proteins, the more repetitive nature of monomeric units that make up nucleic acids limits both the formation of fine structure in folded polynucleotides and the chemical reactivity of RNA and DNA. The fact that a nucleic acid enzyme can co-opt one of the favorite chemical units of protein-based enzymes supports the notion that RNA could rally its limited structure-forming potential and, using the catalytic tools of modem protein enzymes, could produce and maintain a complex metabolic state.

Materials and Methods

In Vitro Selection and Reselection

In vitro selection was carried out essentially as described previously (5,7,47). The initial DNA pool was prepared by PCR amplification of the template 5'-CTAATACGACTCACTATAGGAAGAGATGGCGACA-TCTC(N)$_{40}$GTGAGGTTGGTGTGGTTG (SEQ ID NOs: 53 and 54) (50 pmoles; N an equal probability of occurrence of the four nucleotides) in a 500-μL PCR reaction containing 400 pmoles of primer B2, 5'-biotin-GAATTCTAATACGACTCACTATrA (SEQ ID NO: 55), and 400 pmoles of primer 1, 5'-CAACCACACCAACCTCAC (SEQ ID NO: 56), with 4 thermocycles of 94° C. (15 sec), 50° C. (30 sec), and 72° C. (30 sec). prepared as described previously (16). Amplified DNA was precipitated.with ethanol, resuspended in binding buffer (50 mM HEPES (pH 7.5 at 23° C.), 0.5 M NaCl, 0.5 M KCl, and 0.5 mM EDTA), and the solution was passed through a streptavidin-derivatized affinity matrix to generate immobilized single-stranded DNA[15]. The matrix displaying the pool DNA was repeatedly washed with binding buffer (1.5 mL over 30 min), and subsequently eluted over the course of 1 hr with three 20-μL aliquots of reaction buffer in which HEPES was replaced with 50 mM histidine (pH 7.5, 23° C.). In rounds 8–11, reaction time was reduced to 25–15 min to favor those molecules that cleave more efficiently. Selected DNAs were preciptitated with ethanol and amplified by PCR using primer 1 and primer 2, 5'-GAATTCTAATACGACTCACTATAGGAAGAGATGG-CGAC (SEQ ID NO: 57), and the resulting PCR was reamplified as described above to reintroduce the biotin and embedded ribonucleotide moieties.

Reselection of the class II deoxyribozyme was initiated with a pool of $10^3$ DNAs, each carrying a 39-nucleotide core that had been mutagenized with a degeneracy of 0.21 per position. Similarly, HD2 reselection was conducted with an initial pool in which 26 nucleotides was mutagenized to a degeneracy of 0.33 per position. Individual from the final selected pools were analyzed by cloning and sequencing. The DNA pools were prepared for this process by PCR amplification using primer 2 in place of primer B2. DNA populations and individual precursor DNAs were prepared for assays as described previously (7).

Deoxyribozyme Catalysis Assays

All catalytic assays were conducted in the presence of 0.5 M NaCl, 0.5 M KCl, 0.5 mM EDTA. Single turn-over assays contained a trace amount (~50 nM) substrate oligonucleotide and an excess (1–10 μM) DNA catalyst as described for each assay. The cofactor used was L-histidine unless otherwise stated. Reactions were terminated by addition to an equal volume of a solution containing 95% formamide, 0.05% xylene cyanol, and 0.05% bromophenyl blue and stored on ice prior to gel electrophoresis. Termination buffers containing both urea and EDTA were incapable of completely terminating deoxyribozyme activity.

Caged histidine experiments were conducted with intact dipeptides or with a concentration of hydrolyzed dipeptide products. Hydrolysis of dipeptides was achieved by incubating solutions containing 100 mM dipeptide and 6 N HCl in a sealed tube at 115° C. for 23 hr. Samples were evaporated in vacuo, coevaporated with deionized water, and the resuspended samples were adjusted to neutral pH prior to use.

Catalytic rate constants ($k_{obs}$) either were determined by determining the initial velocity of the reaction (16) or by plotting the natural log of the fraction substrate remaining over time, where the negative slope of the line obtained over several half lives represents $k_{obs}$. The uncatalyzed rate was determined by incubating a trace amount of 5' $^{32}$P-labeled substrate under reaction conditions in the absence of deoxyribozyme at 23° C. or at −20° C. for 21 days. Comparative analysis of RNA phosphoester cleavage indicates that the rate constant for uncatalyzed RNA cleavage in the presence of histidine does not exceed the speed of substrate degradation due to radiolysis. It is expected that the maximum uncatalyzed rate for cleavage of the embedded RNA linkage does not exceed $10^{-8}$ min$^{-1}$. This value is ~10-fold lower than the value obtained in the presence of 1 mM 1 Mg$^{2+}$ (7).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

REFERENCES

1. Beal, P. A. and Dervan, P. B. (1991) *Science* 251, 1360–1363.
2. Berzal-Harranz, A., Joseph, A. and Burke, J. A. (1992) *Genes and Dev.* 6, 129–134.
3. Bock, L. C., Griffin, L. C., Latham, J. A., Vermaas, E. H. and Toole, J. J. (1992) *Nature* 355, 564–566.
3a. P. Boyer, ed. (1970) *The Enzymes*, 3rd ed., vol. 1 Academic Press, New York.
4. Breaker, R. R. (1996) *Curr. Op. Biotech.* 7, 442–448.
5. Breaker, R. R., and Joyce, G. F. (1994) *Chem. & Biol.* 1, 223–229.
6. Breaker, R. R., and Joyce, G. F. (1994) *Trends Biotech.* 12, 268.
7. Breaker, R. R., and Joyce, G. F. (1995) *Chem. & Biol.* 2, 665–660.
8. For reviews, see Cech, C. R. (1990) *Ann. Rev. Biochem.* 59, 543; Symons, R. H. (1992) *Ann. Rev. Biochem.* 61, 641; Altman, S., Kirsebom, L., and Talbot, S. (1995) In: *tRNA: Structure, Biosynthesis, and Function*, D. Söll and U. Raj Bhandary, eds., American Society for Microbiology, Washington, D.C., pp 67–78; Michel F., and Ferat, J.-L. (1995) *Ann. Rev. Biochem.* 64, 435 (1995).
9. Christoffersen, R. E. and Marr, J. J. (1995). *J. Med. Chem.* 38, 2023–2037.
10. Cuenoud, B., and Szostak, J. W. (1995) *Nature* 375, 611–614.
11. Engel, M. H. and Hare, P. E. (1982) *Carnegie Inst. Wash. Yearbook* 81, 422–425.
12. Fedor, M. J. and Uhlenbeck, O. C. (1992) *Biochemistry* 31, 12042.
13. Forster, A. C., and Symons, R. H. (1987) *Cell* 49, 211.
14. Frank-Kamenetskii, M. D. and Mirkin, S. M. (1995) *Annu. Rev. Biochem.* 64, 65–95.
15. Gilbert, W., (1986) *Nature* 319, 618; Hirao, H. and Ellington, A. D., (1995) *Current Biol.* 5, 1017.
16. Gold, L. (1995) *J. Biol. Chem.* 270, 13581–13584.
17. Gold, L., Polisky, B., Uhlenbeck, O., Yarus, M. (1995) *Ann. Rev. Biochem.* 64, 763–797.
18. Hermann, T. and Heumann, H. (1995) *RNA* 1, 1009–1017.
19. Herschlag, D. and Cech, T. R. (1990) *Nature* 344, 405–409.
20. Huizenga, D., E. and Szostak, J. W. (1995) *Biochemistry* 34, 656–665.
21. Jenison, R. D., S. C. Gill, A. Pardi, B. Polisky, (1994) *Science* 263, 1425.
21a. Jose, A. M., Soukup, G. A., and Breaker, R. R. (2001) *Nucleic Acids Res.* 21, 1631–1637.
22. Joshi, R. R., Likhite, S. M., Kumar, R. K. and Ganesh, K. N. (1994) *Biochim. Biophys. Acta* 1199, 285–292.
23. Kazakov, S. A., Astashkina, T. G., Mamaev, S. V. and Vlassov, V. V. (1988). *Nature* 335, 186–188.
23a. Koizumi, M., Kerr, J. K., Soukup, G. A.,and Breaker, R. R. (1999) *Nucleic Acids Symp. Ser.* 42, 275–276.
23b. Koizumi, M., Soukup, G. A. Kerr, J. K., and Breaker, R. R. (1999) *Nature Struct. Biol.* 6, 1062–1071.
24. Li, Y. and Sen, D. (1996) *Nature Struct. Biol.* 3, 743–747
25. Lim, C. and Tole, P. (1992) *J. Am. Chem. Soc.* 114, 7245–7252.
26. Lin, Y., Padmapriya, A., Morden, K. M. and Jayasena, S. D. (1995) *Proc. Natl. Acad. Sci. USA* 92, 11044–11048.
27. Lindahl, T. (1993) *Nature* 362, 709–715.
28. Long, D. M., and Uhlenbeck, O. C., (1994) *Proc. Natl. Acad. Sci. USA* 91, 6977 and references therein; Tuschl, T., and Eckstein, F. (1993) *Proc. Natl. Acad. Sci. U.S.A.* 90, 6991.
29. Moser, H. E. and Dervan, P. B. (1987) *Science* 238, 645–650.
30. Perreault, J. -P. and Altman, S. (1992) *J. Mol. Biol.* 226, 399–409.
31. Perreault, D. M. and Anslyn, E. V. (1997) *Angew. Chem. Int. Ed. Engl.* 36, 432–450.
32. Pley, H. W., K. M. Flaherty, D. B. McKay, *Nature* 372, 68 (1994); T. Tuschl, C. Gohlke, T. M. Jovin, E. Westhof, F. Eckstein, *Science* 266,785 (1994); S. T. Sigurdsson and F. Eckstein, *Trends Biotech.* 13, 286 (1995); W. G. Scott, J. T. Finch, A. Klug, *Cell* 81, 991 (1995).
32a. Porta, H., and Lizardi, P. M. (1995 *Biotechnology* 13, 161–164.
33. Robertson, D. L. and Joyce, G. F. (1990) *Nature* 344, 467–468.
34. SantaLucia Jr., J., Allawi, H. T. and Seneviratne, P. A. (1996) *Biochemistry* 35, 3555–3562.
35. Sassanfar, M., and Szostak, J. W. (1993) *Nature* 364, 550–553 and *Science* 263, 1425–1429.
36. Schultz, P. G., Lerner, R. A. (1995) *Science* 252, 1835–1842.
36a. Seetharaman, S., Zivarts, M., Sudarsan, N., and Breaker, R. R. (2001) *Nature Biotechnol.* 19, 336–341.
37. Serra, M. J., and Turner, D. H. (1995) *Methods Enzymol.* 259, 242.
38. Sigman, D. S. and Chen, C. B. (1990) *Ann. Rev. Biochem.* 59, 207–236.
39. Sigman, D. S., Mazumder, A. and Perrin, D. M. (1993) *Chem. Rev.* 93, 2295–2316.
39a. Soukup, G. A., and Breaker, R. R. (1999) *Proc. Nat. Acad. Sci. USA* 96, 3584–3589.
39b. Soukup, G. A., and Breaker, R. R. (1999) *Structure* 7, 783–791.
39c. Soukup, G. A., and Breaker, R. R. (1999) *Tibtech* 17, 469–476.
39d. Soukup, G. A., DeRose, E., Koizumi, M., and Breaker, R. R. (2001) *RNA* 7, 524–536.
39e. Soukup, G. A., Emilson, G. A., and Breaker, R. R. (2000) *J. Mol. Biol.* 298, 623–632.
40. Strobel, S. A. and Dervan, P. B. (1990) *Science* 249, 73–75.
41. Strobel, S. A. and Dervan, P. B. (1991) *Nature* 350, 172–174.
42. Strobel, S. A. and Dervan, P. B. (1992) *Methods Enzymol.* 216, 309–321.
43. Strobel, S. A. and Doudna, J. A. (1997) *Trends Biochem. Sci.* 22, 262–266.
44. Symons, R. H. (1992) *Ann. Rev. Biochem.* 61, 641–671.
44a. Tang, J., and Breaker, R. R. (1977) *Chem. & Biol.* 4, 453–459.
44b. Tyagi, S., and Kramer, F. R. (1996) *Nature Biotech.* 14 303–308.
45. Walsh, C. (1978) *Enzyme Reaction Mechanisms*, W. H. Freeman and Co., New York.
46. Williamson, J. R. (1994) *Ann. Rev. Biophys. Biomol. Struct.* 23, 703–730.
47. Wladkowski, B. D., Krauss, M. and Stevens, W. J. (1995) *J. Am. Chem. Soc.* 117, 10537–10545.

48. Woese, C. R. and Pace, N. R. (1993) In: *The RNA World*, R. R. Gesteland and J. F. Atkins, eds. Cold Spring Harbor Laboratory Press pp 91–117.
49. Wyatt, J. R., Vickers, T. A., Robertson, J. L., Buckheit, J., R. W., Klimkait, T., DeBaets, E., Davis, P. W., Rayner, B., Imbach, J. L. and Ecker, D. J. (1994) *Proc. Natl. Acad. Sci. USA* 91, 1356–1360.
50. Zuker, M. (1989) *Science* 244, 48–52.

The papers cited herein are expressly incorporated in their entireties by reference.

What is claimed is:

1. A DNA polynucleotide comprising an allosteric site and an enzyme domain spatially distinct from said allosteric site, wherein reversible interaction of a chemical effector with the allosteric site on the DNA polynucleotide reversibly alters the cleavage function or configuration of the DNA polynucleotide, wherein the chemical effector is a metal ion or a small molecule having a molecular weight of 300 Daltons or less.

2. The DNA polynucleotide according to claim 1 wherein the function or configuration of the DNA polynucleotide is altered in less than 60 minutes after interaction with the chemical effector.

3. A DNA polynucleotide comprising an allosteric site and an enzyme domain spatially distinct from said allosteric site, wherein the rate of catalysis of the enzyme domain is reversibly modulated by interaction with a chemical effector, wherein the chemical effector is a metal ion or a small molecule having a molecular weight of 300 Daltons or less.

4. The DNA polynucleotide according to claim 3 wherein an observable change in the rate of catalysis of the enzyme domain occurs in less than 6 minutes of interaction with the chemical effector.

5. The DNA polynucleotide according to claim 4 wherein the observable change occurs in less than 1 minute.

6. The DNA polynucleotide according to claim 1 or 3 wherein the chemical effector is selected from the group consisting of amino acids, amino acid derivatives, peptides, nucleosides, nucleotides, and steroids.

7. A biosensor comprising the DNA polynucleotide according to claim 1 or 3.

8. A method for detecting the presence or absence of a compound or its concentration in a sample comprising contacting the sample with a DNA polynucleotide comprising an allosteric site and an enzyme domain spatially distinct from said allosteric site, wherein reversible interaction of the compound with the allosteric site alters the cleavage function or configuration of the polynucleotide relative to that of a control sample, and observing said alteration in the function or configuration of the DNA polynucleotide, wherein the chemical effector is a metal ion or small molecule having a molecular weight of 300 Daltons or less, and further wherein an alteration in function or configuration of the DNA polynucleotide indicates the presence or absence of a compound or its concentration in the sample.

9. The method according to claim 8 wherein the presence or absence of a compound or its concentration is detected by observation of an alteration in the cleavage function of the polynucleotide.

10. The method according to claim 8 wherein the chemical effector is selected from the group consisting of amino acids, amino acid derivatives, peptides, nucleosides, nucleotides, and steroids.

11. The DNA polynucleotide according to claim 3 wherein the rate of catalysis of the enzyme is measured by observing enzyme self-cleavage or substrate cleavage.

12. The biosensor according to claim 7, wherein the DNA polynucleotide is attached to a solid support.

13. An RNA polynucleotide comprising an allosteric site and an enzyme domain spatially distinct from said allosteric site, having three stem components, stem I, stem II and stem III, wherein stem I and stem III are polynucleotide sequences which together form the enzyme domain and stem II is a polynucleotide sequence which forms the allosteric site, wherein interaction of a chemical effector with the allosteric site reversibly alters the cleavage function or configuration of the polynucleotide, further wherein the chemical effector is a metal ion or a small molecule having a molecular weight of 300 Daltons or less.

14. The polynucleotide according to claim 13 wherein the cleavage function or configuration of the polynucleotide is altered in less than 60 minutes after interaction with the chemical effector.

15. An RNA polynucleotide comprising an allosteric site and an enzyme domain spatially distinct from said allosteric site, having three stem components, stem I, stem II and stem III, wherein stem I and stem III are polynucleotide sequences which together form the enzyme domain and stem II is a polynucleotide sequence which forms the allosteric site, wherein interaction of a chemical effector with the allosteric site reversibly modulates the rate of catalysis of the polynucleotide, further wherein the chemical effector is a metal ion or a small molecule having a molecular weight of 300 Daltons or less.

16. The polynucleotide according to claim 15 wherein an observable change in the rate of catalysis of the polynucleotide occurs in less than 6 minutes of interaction with the chemical effector.

17. The polynucleotide according to claim 16 wherein the observable change occurs in less than 1 minute.

18. The polynucleotide according to claim 15 wherein the chemical effector is selected from the group consisting of amino acids, amino acid derivatives, peptides, nucleosides, nucleotides, and steroids.

19. A biosensor comprising the polynucleotide according to claim 13 or 15.

20. A method for detecting the presence or absence of a compound or its concentration in a sample comprising contacting the sample with a polynucleotide according to claim 13 or 15, such that reversible interaction of the compound with the allosteric site alters the cleavage function or configuration of the polynucleotide relative to that of a control sample, and observing said alteration in the cleavage function or configuration of the polynucleotide, wherein the compound is a chemical effector that is a metal ion or small molecule having a molecular weight of 300 Daltons or less and further wherein an alteration in function or configuration of the polynucleotide indicates the presence or absence of a compound or its concentration in the sample.

21. The method according to claim 20 wherein the presence or absence of a compound or its concentration is detected by observation of an alteration in the cleavage function of the polynucleotide.

22. The method according to claim 20 wherein the compound is a chemical effector that is selected from the group consisting of amino acids, amino acid derivatives, peptides, nucleosides, nucleotides, and steroids.

23. A polynucleotide according to claim 15 wherein the rate of catalysis of the enzyme is measured by observing enzyme self-cleavage or substrate cleavage.

24. A biosensor according to claim 19, wherein the polynucleotide is attached to a solid support.

* * * * *